(12) United States Patent
Won

(10) Patent No.: US 10,311,343 B2
(45) Date of Patent: Jun. 4, 2019

(54) APPARATUS AND METHOD FOR SURFACE AND SUBSURFACE TACTILE SENSATION IMAGING

(71) Applicant: TEMPLE UNIVERSITY—Of The Commonwealth System of Higher Education, Philadelphia, PA (US)

(72) Inventor: Chang-Hee Won, Maple Glen, PA (US)

(73) Assignee: TEMPLE UNIVERSITY—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 15/914,317

(22) Filed: Mar. 7, 2018

(65) Prior Publication Data

US 2018/0330208 A1 Nov. 15, 2018

Related U.S. Application Data

(62) Division of application No. 15/593,637, filed on May 12, 2017, now abandoned, which is a division of (Continued)

(51) Int. Cl.
*A61B 5/00* (2006.01)
*G06K 9/78* (2006.01)
(Continued)

(52) U.S. Cl.
CPC .............. *G06K 9/78* (2013.01); *A61B 5/0053* (2013.01); *A61B 5/442* (2013.01); *A61B 5/444* (2013.01);
(Continued)

(58) Field of Classification Search
None
See application file for complete search history.

(56) References Cited

U.S. PATENT DOCUMENTS 6,218,673 B1 4/2001 Gore et al.
2003/0164954 A1 9/2003 Gerhard et al.
(Continued)

OTHER PUBLICATIONS

Hosseini, et al., "A medical tactile sensing instrument for detecting embedded objects, with specification application for breast examination", The International Journal of Medical Robotics and Computer Assisted Surgery, 2010; 6: 73-82.
(Continued)

*Primary Examiner* — Jerry Rahll
(74) *Attorney, Agent, or Firm* — Drinker Biddle & Reath LLP

(57) ABSTRACT

A tactile sensor, computer readable medium, methods of using and manufacturing the tactile sensor, and methods and apparatuses for processing the information generated by the tactile sensor. The tactile sensor includes a planar optical waveguide comprised of a flexible and transparent layer; a light configured to direct light into the optical waveguide; a light sensor or an imager facing the optical waveguide and configured to generate signals from light scattered out of the optical waveguide; and a controller which may be configured to generate an image of the object and characteristics of the object. The waveguide may be configured so that some of the light directed into the optical waveguide is scattered out of the waveguide if the waveguide is deformed by being pressed against the object. A finite element and a neural network are used to estimate mechanical characteristics of the objects.

24 Claims, 21 Drawing Sheets

Related U.S. Application Data application No. 13/702,042, filed as application No. PCT/US2011/043203 on Jul. 7, 2011, now Pat. No. 9,652,696.

(60) Provisional application No. 61/363,062, filed on Jul. 9, 2010.

(51) Int. Cl.

| | |
|---|---|
| *G02B 6/12* | (2006.01) |
| *G01L 1/24* | (2006.01) |
| *F21V 8/00* | (2006.01) |
| *G06F 3/01* | (2006.01) |
| *H04N 7/18* | (2006.01) |
| *G06F 3/041* | (2006.01) |

(52) U.S. Cl.
CPC ............ *G01L 1/247* (2013.01); *G02B 6/0013* (2013.01); *G02B 6/0045* (2013.01); *G02B 6/12002* (2013.01); *A61B 5/0077* (2013.01); *A61B 5/7267* (2013.01); *A61B 2562/0233* (2013.01); *G01L 1/24* (2013.01); *G06F 3/016* (2013.01); *G06F 3/0414* (2013.01); *H04N 7/18* (2013.01)

(56) References Cited

U.S. PATENT DOCUMENTS

| | | |
|---|---|---|
| 2006/0152885 A1 | 7/2006 | Hewit et al. |
| 2006/0173319 A1 | 8/2006 | Sumi |
| 2007/0213617 A1 | 9/2007 | Berman et al. |
| 2008/0179507 A2 | 7/2008 | Han |
| 2008/0284925 A1 | 11/2008 | Han |

OTHER PUBLICATIONS

Lee, et al., "High Resolution Tactile Imaging Sensor using Total Internal Reflection and Non-rigid Pattern Matching Algorithm", Sensors Journal, IEEE 11(9): 284-2093 (published on-line Jan. 28, 2011).

Lee, et al., "Design and Evaluation of an Optical Tactile Imaging Device for Tumor Detection", 52nd Annual Meeting of American Association of Physicists and Medicine (AAPM), Philadelphia, PA, Jul. 18-22, 2010.

Lee, et al., "Tactile sensation imaging for artificial palpation", Eurohaptics Jul. 8-10, 2010, Amsterdam.

Lee, et al., "Tactile Imaging Sensor for Subsurface Tumor Detection in Prostate Phantom", The First AMA-IEEE Medical Technology Conference on Individualized Healthcare, Washington, DC, Mar. 21-23, 2010.

Lee, et al., "Tactile sensation imaging system for inclusion characterization", Proc. SPIE 7890, Advanced Biomedical and Clinical Diagnostic Systems IX, 78901D (Feb. 21, 2011).

Lee, et al., "Design and Evaluation of an Optical Tactile Imaging Device for Tumor Detection", Abstract ID13673, 52nd Annual AAPM Meeting (Jul. 18, 2010).

Ohka, et al., "An Experimental Optical Three-axis Tactile Sensor Featured with Hemispherical Surface", Trans. Jpn. Soc. Mech. Eng., vol. 74, No. 742, C (2008), pp. 1477-1484.

Saga, et al., "High-resolution tactile sensor using the deformation of a reflection image", Sensor Review 27.1 (2007): 35-42.

Shen, et al., "Quantification and Verification of Automobile Interior Textures by a High Performance Tactile-Haptic Interface", Proceedings of the 2006 IEEE/RSJ, International Conference on Intelligent Robots and Systems, Oct. 9-15, 2006, Beijing, China.

Zhang, et al., A Multi-Purpose Tactile Sensor Inspired by Human Finger for Texture and Tissue Stiffness Detection, Proceedings of the 2006 IEEE International Conference on Robotics and Biomimetics, Dec. 17-20, 2006, Kunming, China.

| Number | True size (d) | Est. size (d) | Error |
|---|---|---|---|
| 1 | 2 mm | 4.11 mm | 105.5% |
| 2 | 8 mm | 8.11 mm | 1.37% |
| 3 | 13 mm | 10.73 mm | 17.46% |
| 4 | 7 mm | 5.77 mm | 17.57% |
| 5 | 7 mm | 4.91 mm | 29.85% |
| 6 | 7 mm | 4.94 mm | 29.43% |
| 7 | 10 mm | 10.11 mm | 1.1% |
| 8 | 10 mm | 10.74 mm | 7.4% |
| 9 | 10 mm | 10.57 mm | 5.7% |
| Mean | 8.22 mm | 7.76 mm | 23.93% |
| Std. | 3.07 mm | 2.84 mm | 32.47% |

FIG. 15A

| Number | True depth (h) | Est. depth (h) | Error |
|---|---|---|---|
| 1 | 5 mm | 8.52 mm | 70.4% |
| 2 | 5 mm | 7.06 mm | 41.2% |
| 3 | 5 mm | 5.81 mm | 16.2% |
| 4 | 4 mm | 7.97 mm | 99.25% |
| 5 | 8 mm | 8.23 mm | 2.86% |
| 6 | 12 mm | 8.45 mm | 29.58% |
| 7 | 5 mm | 6.29 mm | 25.8% |
| 8 | 5 mm | 6.11 mm | 22.2% |
| 9 | 5 mm | 7.33 mm | 46.6% |
| Mean | 6 mm | 7.31 mm | 39.34% |
| Std. | 2.5 mm | 1.05 mm | 29.68% |

FIG. 15B

| Number | True modulus (E) | Est. modulus (E) | Error |
|---|---|---|---|
| 1 | 120 kpa | 74.52 kPa | 37.9% |
| 2 | 120 kpa | 83.97 kPa | 30% |
| 3 | 120 kpa | 79.46 kPa | 33.78% |
| 4 | 100 kpa | 78.29 kPa | 21.71% |
| 5 | 100 kpa | 78.06 kPa | 21.94% |
| 6 | 100 kpa | 77.87 kPa | 22.13% |
| 7 | 40 kpa | 84.84 kPa | 112.1% |
| 8 | 70 kpa | 76.96 kPa | 17.79% |
| 9 | 100 kpa | 82.21 kPa | 34.15% |
| Mean | 96.67 kPa | 79.57 kPa | 34.14% |
| Std. | 26.45 kPa | 3.41 kPa | 30.43% |

FIG. 15C

APPARATUS AND METHOD FOR SURFACE AND SUBSURFACE TACTILE SENSATION IMAGING

CROSS-REFERENCE TO RELATED APPLICATIONS

This application is a divisional of U.S. patent application Ser. No. 15/593,637, filed May 12, 2017, which is a divisional of U.S. patent application Ser. No. 13/702,042 (U.S. Pat. No. 9,652,696), which is a national stage of PCT/US2011/043203, filed 7 Jul. 2011. This application claims the benefit of U.S. Provisional Application No. 61/363,062 filed Jul. 9, 2010. The entire disclosure of those applications is incorporated herein by reference.

FIELD OF INVENTION

The invention relates to a tactile sensor, methods of using and manufacturing the tactile sensor, and methods and apparatuses for processing the information generated by the tactile sensor, and more specifically to tactile sensors that utilize a flexible optical waveguide that uses scattered light for determining properties of surface materials and subsurface inclusions.

BACKGROUND OF THE INVENTION

In the discussion of the background that follows, reference is made to certain structures and/or methods. However, the following references should not be construed as an admission that these structures and/or methods constitute prior art. Applicants expressly reserve the right to demonstrate that such structures and/or methods do not qualify as prior art.

Detecting and diagnosing subsurface inclusions such as tumors and lumps is a difficult problem. For example, breast or mammary tumors or lumps, or prostate tumors and lumps may be very difficult to detect particularly in the early stages of development. Many imaging devices are available for detecting and diagnosing tumors such as computer tomography (CT), mammogram, ultrasonic imaging, and magnetic resonance imaging (MRI). However, each of these technologies has its disadvantages, for example MRI is relatively expensive and has low specificity; CT and mammogram expose the patient to known dangers of ionized radiation; ultrasound has relatively low contrast, low resolution and low signal to noise ratio.

There are no real good screening tools with high sensitivity and specificity for cancer screening. Sensitivity is defined as the percentage of sick people who are identified as being sick, and specificity is defined as the percentage of healthy people who are identified as being healthy. According to one study, a clinical breast examination has a sensitivity of 54% and a specificity of 94%. See Jatoi 2003. Doppler ultrasound has a sensitivity of 68% and a specificity of 95%. See Raza, et al. 1997. MRI has a sensitivity of 88.1% and a specificity of 67.7%. See Bluemke et al., 2004. Mammography has a sensitivity of 68.6% and a specificity of 94.4%. See Carney, et al. 2003.

Each of the imaging devices mentioned above has difficulty determining how rigid (or elastic) a tumor or lump is. However, there have been studies linking stiffness of the tumor with the cancerous tissues. See Regini, et al. 2010, Wellman, et al. 2001, and Greenleaf, et al. 2003. Moreover, plaque lined blood vessels are less elastic than normal vessels. Thus, stiffness is an important characteristic in determining whether tissue is unhealthy. Furthermore, health care providers often use their finger to probe the tumor or lump to try and determine whether the tumor or lump is rigid; however, the human finger is limited in its ability to determine how rigid a tumor or lump is particularly when the tumor or lump may be relatively deep within the patient's tissue. For example, a lump may be near the chest with several inches of breast tissue between the health care provider's finger and the lump. There is a need for a device that can quantify and display the stiffness of the tumor with greater accuracy than the human finger.

Additionally, when a tumor or lump is detected, the health care provider must determine whether the tumor or lump is benign or cancerous. Currently, an invasive biopsy is typically performed to determine whether or not a tumor is malignant. However, a screening device that can distinguish between a malignant and benign tumor would be extremely useful for early detection. Some progress has been made in determining whether a tumor or lump is benign or cancerous based on properties such as tissue elasticity. See Wilson, et al. 2000, Greenleaf, et al. 2003, and Wellman, et al. 1999. Cancerous lumps tend to be more rigid. More recently, sono-elastography reported a 88.5% sensitivity and 92.7% specificity in diagnosing nodular breast lesions using tissue elasticity. See Regini, et al. 2010. Perhaps more importantly, the same paper noted that out of 120 cases, 116 malignancy cases were correctly identified by the elasticity scores. Thus stiffness of the tumor is a good indicator of the malignancy of the tumor.

There are a few methods for determining the elasticities of tumors. For example, tactile sensors, piezoelectric finger sensor (PEF), and elastography. The artificial tactile sensing methods disclosed in Dargahi, et al. 2004, and Najarian et al. 2009, and the tactile imaging method disclosed in Gaela 2004, use a transduction method to estimate the stress information and obtain elasticity data using a computational model. Commercial palpation imaging systems are available from companies such as Medical Tactile™ Inc. and Assurance Medical™ Inc. These sensors use hundreds of transducer sensors to display the breast examination information. These sensors are used to detect the force applied to the tissue, which is used to calculate the stress. Calculating the stress is necessary to calculate the elasticity of lump or tumor.

Young's modulus (i.e., elasticity) can also be computed from MRI elastography. Also, atomic force microscopy has been used to detect elasticity; however, this is for small local area elasticity measurements. See Vinckier, et al 1998. Both MRI and atomic force microscopy are extremely expensive and cumbersome.

A piezoelectric finger sensor disclosed in U.S. Pat. No. 7,497,133, issued to Shih et al., also can determine the Young's modulus and shear modulus of the contacted objects. A method is disclosed in Shih that uses the piezoelectric finger to apply a force, and then the corresponding displacement is determined by the piezoelectric sensor. However, this method suffers from piezoelectric sensor nonlinearity, hysteresis, and a difficulty in calibrating the piezoelectric finger.

Another approach that detects the elasticity sensations of the organs is elastography. This approach attempts to determine the relative stiffness or elasticity of tissue by using ultrasonic imaging techniques while vibrating the tissue at low frequencies. See Insana, et al. 2004. The research with ultrasound elastography shows that strain information has the potential of distinguishing malignant and benign tumors. See Garra, et. al 1997, Stravos, et al 1993, and Hall 2003.

This method includes emitting ultrasonic waves along a path into the tissue and detecting an echo sequence resulting from the ultrasonic wave pulse. However, ultrasound elastography suffers from limited contrast, resolution and low signal to noise problems.

Therefore, there is a need in the art for an apparatus and method for tactile sensor for generating an image of an object.

SUMMARY OF THE INVENTION

It is to be understood that both the foregoing general description and the following detailed description are exemplary and explanatory and are intended to provide further explanation of the invention as claimed.

A tactile sensor for generating an image of an object is disclosed. The tactile sensor may include a planar optical waveguide comprised of a first layer and second layer that are flexible and transparent. The second layer may be less flexible than the first layer and the refractive index of the second layer may be less than the refractive index of the first layer. The tactile sensor may include at least one source of light configured to direct light into the optical waveguide; and a light sensor facing the optical waveguide and configured to generate signals from light scattered out of the optical waveguide. The waveguide may be configured so that at least some of the light directed into the optical waveguide is scattered out of the first layer when the first layer is deformed, and at least some of the light directed into the optical waveguide is scattered out of the second layer when the second layer is deformed. The first layer and the second layer may be deformed by the tactile sensor being pressed against the object.

The planar optical waveguide may be transparent.

The tactile sensor may include an opaque frame for supporting the transparent planar optical waveguide around a circumference of the optical waveguide.

The tactile sensor may include a rigid layer that is substantially rigid and transparent. The rigid layer may be between the light sensor and the optical waveguide. The optical waveguide may press against the rigid layer. The rigid layer may have a refractive index less than the optical waveguide.

The rigid layer may be composed of glass.

The tactile sensor may include a lens between the optical waveguide and the light sensor to focus the scattered light onto the light sensor.

The optical waveguide may be in the shape of, for example, one of: a sheet, an oval, or a disk.

The tactile sensor may include a third layer that is flexible and transparent, wherein the third layer is less flexible than the second layer, and the refractive index of the third layer is less than the refractive index of the second layer.

The modulus of elasticity of the third layer may be approximately $3.4 \times 10^4$.

The refractive index of the third layer may approximately 1.39.

The modulus of elasticity of the second layer may be approximately $8.0 \times 10^4$ Pa and the modulus of elasticity of the first layer (outer layer) is approximately $1.4 \times 10^5$ Pa.

The refractive index of the second layer may be approximately 1.40, and the refractive index of the first layer is approximately 1.41.

The optical waveguide may have at least four sides. The at least one source of light may include at least one source of light configured to direct light into at least four sides of the optical waveguide.

The first layer and the second layer may be substantially composed of polydimethylsiloxane.

The light source may be arranged such that the directed light travels through the first layer and the second layer by substantially total internal reflection.

The light source may be configured to emit light in a spatial radiation pattern with an angle less than a maximum angle under which the emitted light directed into the waveguide remains trapped in the waveguide by total internal reflection.

The object may be a subsurface inclusion and the inclusion is one of a tumor or a lump.

The tactile sensor may include a controller. The controller may be configured to display an image of the object based on the signals from the light sensor.

The controller may be configured to generate a two or three dimensional image of the object based on determining from the signals from the light sensor an intensity of scattered light striking a portion of the light sensor corresponding to the object.

The controller may be configured to calculate a size of the object.

The controller may be configured to calculate a shape of the object.

The controller may be configured to calculate a depth of the object.

The controller may be configured to calculate a diameter of the object.

The controller may be configured to diagnose the object based on a ratio of a calculated Young's Modulus to a calculated shear modulus.

The controller may be configured to generate an image of the object based on determining from the signals from the light sensor an intensity of scattered light striking a portion of the light sensor corresponding to the object. A pixel having a greater pixel intensity may indicate the pixel being closer to a centroid of the image of the object and a lesser pixel intensity may indicate the pixel being farther away from the centroid of the image of the object.

The controller may be configured to compare a captured first image of the object having a first force applied to the object with a captured second image of the object having a second force applied to the object, and configured to calculate the Young's Modulus of the object based on comparing the object in the first image with the object in the second image and based on the first force and the second force.

The controller may be configured to compare a captured first image of the object having a first force applied to the object with a captured second image of the object having a second force applied to the object, and configured to calculate the shear modulus of the object based on comparing the object in the first image with the object in the second image and based on the first force and the second force.

The controller may be configured to compare a captured first image of the object having a first force applied to the object with a captured second image of the object having a second force applied to the object, and configured to calculate the elasticity of the object based on comparing the object in the first image with the object in the second image and based on the first force and the second force.

A size of the first force and a size of the second force may be calculated based on determining from the generated signals from the light sensor an intensity of scattered light striking a portion of the light sensor corresponding to the object.

The controller may be configured to compare the captured first image of the object with the captured second image of the object by: matching the object in the first image with the object in the second image; and comparing the object in the first image with the matched object in the second image. The controller may be configured to calculate an elasticity of the object by: calculating the deformation of the object in the second image based on comparing the object in the first image with the object in the second image; and calculating the elasticity of the object based on a size of the first force and based on a size of the second force and based on the calculated deformation of the object in the second image compared to the object in the first image by tracking a change in a position of control points selected from the first image and the second image.

The controller may be configured for calculating the deformation of the object by: calculating the deformation of the object in the second image based on comparing the object in the first image with the object in the second image by measuring the change in position of control points chosen from the first image and the second image.

The width of the transparent planar optical waveguide may be, for example, from 2 millimeters to 3 centimeters long.

The controller may be further configured to display at least one of an elasticity of the object, a size of the object, a shape of the object, a Young's modulus of the object, a shear modulus of the object, and a malignancy determination of the object.

A tactile sensor for generating an image of an object is disclosed. The tactile sensor may include, for example, a planar optical waveguide comprised of a first layer that is flexible and transparent; at least one source of light configured to direct light into the optical waveguide; a light sensor facing the optical waveguide and configured to generate signals from light scattered out of the optical waveguide; and a controller, the controller configured to display an image of the object based on the signals from the light sensor. The waveguide may be configured so that at least some of the light directed into the optical waveguide is scattered out of the first layer. The first layer may be deformed by the tactile sensor being pressed against the object. The controller may be configured to generate an image of the object based on determining from the signals from the light sensor an intensity of scattered light striking a portion of the light sensor corresponding to the object. A greater pixel intensity may indicate being closer to a centroid of the object and a lesser pixel intensity may indicate being farther away from the centroid.

In embodiments, the planar optical waveguide is transparent.

The controller may be configured to generate a two or three dimensional image of the object based on determining from the signals from the light sensor an intensity of scattered light striking a portion of the light sensor corresponding to the object.

The controller may be configured to compare a captured first image of the object having a first force applied to the object with a captured second image of the object having a second force applied to the object, and configured to calculate the elasticity of the object based on comparing the object in the first image with the object in the second image and based on the first force and the second force.

A size of the first force and a size of the second force may be calculated based on determining from the generated signals from the light sensor an intensity of scattered light striking a portion of the light sensor corresponding to the object.

A tactile sensor for generating an image of an object is disclosed. The tactile sensor including a planar optical waveguide comprised of a first layer that is flexible and transparent; at least one source of light configured to direct light into the optical waveguide; a light sensor facing the optical waveguide and configured to generate signals from light scattered out of the optical waveguide; and a controller, the controller configured to forward the signals from the light sensor to a computer configured to generate an image of the object based on determining from the signals from the light sensor an intensity of scattered light striking a portion of the light sensor corresponding to the object. The waveguide may be configured so that at least some of the light directed into the optical waveguide is scattered out of the first layer, wherein the first layer is deformed by the tactile sensor being pressed against the object.

The waveguide may be transparent.

A method for calculating an elasticity of an object with a tactile sensor is disclosed. The method including receiving a two or three dimensional reconstructed first image of an object having a first force applied, and a two or three dimensional reconstructed second image of the object having a second force applied; calculating a point correspondence between the first image of the object and the second image of the object; calculating a transformation function using the calculated point correspondence; calculating the strain using the calculated transformation function; and calculating the elasticity of the object.

The calculated elasticity of the object may be at least one of: Young's Modulus or shear modulus.

A method for calculating an elasticity of an object with a tactile sensor is disclosed. The method including capturing a first image of an object with a tactile sensor having a first force applied to the object; capturing a second image of the object with a tactile sensor having a second force applied to the object; calculating a stress placed on the object in the first image and a stress placed on the object in the second image; calculating a strain placed on the object using the first image and the second image; and calculating an elasticity of the object.

The calculated elasticity of the object is shear modulus when the first force and the second force are horizontally applied to the object.

The calculated elasticity of the object is Young's Modulus when the first force and the second force are vertically applied to the object.

A method of generating an image of an object is disclosed. The method including directing light into an optical flexible waveguide; pressing an optical flexible waveguide into the object; generating signals from the directed light that is scattered out of the optical flexible waveguide by the optical flexible waveguide deforming from the pressing; and generating an image of the object based on determining from the generated signals an intensity of scattered light scattered out of the waveguide from the pressing.

A greater pixel intensity may indicate being closer to a center of the object and a lesser pixel intensity indicates being farther away from the center of the object.

The method claim may include applying a first force to the object; capturing a first image of the object; applying a second force to the object; capturing a second image of the object; comparing the first image with the second image; matching the object in the first image with the object in the second image; calculating a deformation of the object by comparing the matched object in the first image with the matched object in the second image; and calculating an elasticity object based the calculated deformation and the first force and the second force.

The method may include calculating a size of the first force and a size of the second force based on determining from the generated signals an intensity of the scattered light from the object deforming the waveguide.

A tactile sensor for generating an image of an object is disclosed. The tactile sensor including a planar optical waveguide comprised of a first layer that is flexible and transparent; at least one source of light configured to direct light into the optical waveguide; a light sensor facing the optical waveguide and configured to generate signals from light scattered out of the optical waveguide; and a controller, the controller configured to display an image of the object based on the signals from the light sensor, wherein the waveguide is configured so that at least some of the light directed into the optical waveguide is scattered out of the first layer, wherein the first layer is deformed by the tactile sensor being pressed against the object. The controller may be configured to generate an image of the object based on determining from the signals from the light sensor an intensity of scattered light striking a portion of the light sensor corresponding to the object. The controller may be configured to calculate a force applied to the object by the optical waveguide being pressed into the object based on the intensity of scattered light.

The waveguide may be transparent.

A method of training a neural network to determine inclusion parameters from data gathered from a tactile sensor is disclosed.

The method includes the steps of training the neural network with data generated using a "3" dimensional finite element method ("3D FEM"); and determining a transformation between 3D FEM data of a model of the tactile sensor and actual tactile sensor data.

The data generated using the 3D FEM may comprise a deformed shape of the tactile sensor for different parameters of the inclusion.

The neural network may comprises a first layer with a sigmoid activation function, a second layer with a sigmoid activation function, and a third layer with a linear activation function.

The step of determining a transformation may comprise gathering data generated from pressing the tactile sensor against a manufactured simulated tissue with manufactured inclusions having parameters embedded in the manufactured simulated tissue; and determining a transformation between 3D FEM data of a model of the tactile sensor and actual tactile sensor data by comparing the gathered data with the data generated using the 3D FEM.

The tactile sensor may comprises a first layer and second layer that are flexible and transparent. The second layer may be less flexible than the first layer and the refractive index of the second layer may be less than the refractive index of the first layer.

The tactile sensor may comprise an opaque frame for supporting the transparent planar optical waveguide around a circumference of the optical waveguide.

The controller may be configured to calculate a characteristic of the object by: transforming data gathered from the tactile sensor to values for a model of the tactile sensor; and inputting the transformed data to a neural network to obtain as output estimated characteristics of the object, wherein the neural network was trained using data from the model.

The model may be a "3" dimensional finite element method ("3D FEM").

The characteristics may include at least one of: size, depth, mobility, shape, and elasticity.

The controller may further be configured to estimate a shape of the inclusion based on segmenting a captured image of the object and including portions of the captured image as part of the shape of the object based on a predetermined threshold value.

The controller may further be configured to calculate a first centroid of the object in a captured first image and calculate a second centroid of the object in a captured second image of the object, and configured to calculate a mobility of the object based on a difference between the first centroid and the second centroid.

A non-transitory computer program product is disclosed. The non-transitory computer product may comprise a computer usable medium having a computer readable program code embodied therein, said computer readable program code adapted to be executed to implement a method for calculating an elasticity of an object with a tactile sensor.

The method for calculating an elasticity of an object with a tactile sensor may comprise receiving a two or three dimensional reconstructed first image of an object having a first force applied, and a two or three dimensional reconstructed second image of the object having a second force applied; calculating a point correspondence between the first image of the object and the second image of the object; calculating a transformation function using the calculated point correspondence; calculating the strain using the calculated transformation function; and calculating the elasticity of the object.

A non-transitory computer program product is disclosed. The non-transitory computer program product may comprise a computer usable medium having a computer readable program code embodied therein, said computer readable program code adapted to be executed to implement a method for calculating an elasticity of an object with a tactile sensor.

The method for calculating an elasticity of an object may comprise receiving a first image of an object with a tactile sensor having a first force applied to the object; receiving a second image of the object with a tactile sensor having a second force applied to the object; calculating a stress placed on the object in the first image and a stress placed on the object in the second image; calculating a strain placed on the object using the first image and the second image; and calculating an elasticity of the object.

A non-transitory computer program product is disclosed. The non-transitory computer program product may comprise a computer usable medium having a computer readable program code embodied therein, said computer readable program code adapted to be executed to implement a method to calculate a characteristic of an object.

The method to calculate a characteristic of an object may comprise transforming data gathered from the tactile sensor to values for a model of the tactile sensor; and inputting the transformed data to a neural network to obtain as output estimated characteristics of the object, wherein the neural network was trained using data from the model.

A method of calculating a characteristic of an object is disclosed. The method may comprise transforming data gathered from the tactile sensor to values for a model of the tactile sensor; and inputting the transformed data to a neural network to obtain as output estimated characteristics of the object, wherein the neural network was trained using data from the model.

The optical waveguide of the tactile sensor may be in the shape of one of: a sheet, an oval, a polygon, or a disk.

The optical waveguide of the tactile sensor may be in the shape of a polygon with three or more sides, and wherein the at least one source of light comprises: at least one source of light configured to direct light into the at least three or more sides of the optical waveguide.

A method for calculating an elasticity of an object with a tactile sensor is disclosed. The method may comprise receiving a two or three dimensional reconstructed first image of an object having a first force applied, and a two or three dimensional reconstructed second image of the object having a second force applied; calculating a point correspondence between the first image of the object and the second image of the object; calculating a transformation function using the calculated point correspondence; calculating a strain of the object using the calculated transformation function; and calculating the elasticity of the object.

In embodiments, a width and a length of the planar optical waveguide of the tactile sensor may vary from 2 millimeters to 50 centimeters.

The controller may be configured to generate a two or three dimensional image of the object based on determining from the signals from the light sensor an intensity of scattered light striking a portion of the light sensor corresponding to the object.

The controller may be configured to generate an image of the object based on determining from the signals from the light sensor an intensity of scattered light striking a portion of the light sensor corresponding to the object. A pixel having a greater pixel intensity may indicate the pixel is closer to a centroid of the image of the object and a lesser pixel intensity may indicate the pixel being farther away from the centroid of the image of the object.

The controller may be configured to generate an image of the object based on determining from the signals from the light sensor an intensity of scattered light striking a portion of the light sensor corresponding to the object. The controller may determine that a pixel having a greater pixel intensity indicates at least one of: the pixel is closer to a centroid of the image of the object, an elasticity of a portion of the object corresponding to the greater pixel intensity is less than an elasticity of a portion of the object corresponding to a lesser pixel intensity, or the portion of the object corresponding to the greater pixel intensity is closer to a surface than the portion of the object corresponding to a lesser pixel intensity; and a lesser pixel intensity indicates at least one of: the pixel is farther away from the centroid of the image of the object, an elasticity of the portion of the object corresponding to the lesser pixel intensity is greater than an elasticity of the portion of the object corresponding to a greater pixel intensity, or the portion of the object corresponding to the lesser pixel intensity is farther from a surface than the portion of the object corresponding to a greater pixel intensity.

The controller may further be configured to display at least one of: an elasticity of the object, a size of the object, a shape of the object, a Young's modulus of the object, a shear modulus of the object, a malignancy determination of the object, and a mobility of the object.

The tactile sensor may include a planar optical waveguide comprised of at least a first layer that is flexible and transparent.

The rigid layer of the tactile sensor may be plastic.

DESCRIPTION OF FIGURES

The following detailed description can be read in connection with the accompanying drawings in which like numerals designate like elements, and in which:

FIGS. 15A, 15B, and 15C illustrate a table to validate the method of FIG. 11.

DETAILED DESCRIPTION OF THE INVENTION

"May be" is used to describe exemplary embodiments of the invention and is intended to be used to describe embodiments of the invention without limiting the invention to the described embodiments.

Figure 1:
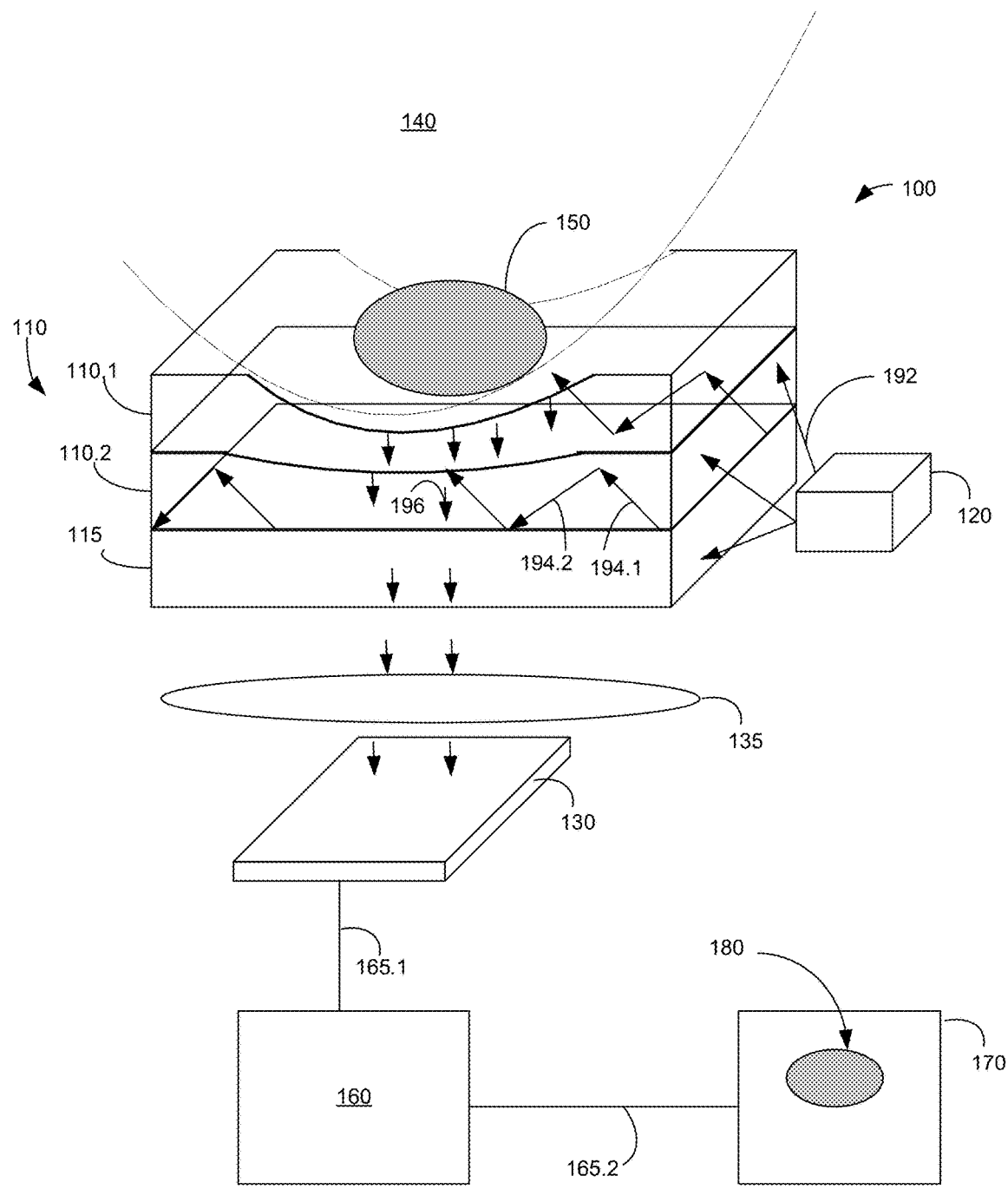
FIG. 1 illustrates an embodiment of a tactile sensor for generating an image of a object.

FIG. 1 illustrates an embodiment of a tactile sensor for generating an image of an object. The tactile sensor 100 includes an optical waveguide 110, which includes a first layer 110.1, a second layer 110.2, a rigid layer 115, a source of light 120, a light sensor 130, and a lens 135. Also, illustrated in FIG. 1 is tissue 140, with an object 150, which in this case is a subsurface inclusion. Additionally, illustrated in FIG. 1 is a controller 160, communication links 165, and a display 170, which as illustrated displays an image 180 of the object 150. In embodiments, the controller 160 and/or the display 170 may be part of the tactile sensor 100. When the tactile sensor 100 is pressed against tissue 140, the optical waveguide 110 is deformed causing light 194 to be scattered from the optical waveguide 110. The scattered light 196 strikes the light sensor 130. The light sensor 130 generates signals that are communicated to the controller 160. The controller 160 is configured to take the signals and generate an image 180 of the object 150, which the controller 160 displays on the display 170.

The optical waveguide 110 may include a first layer 110.1 and a second layer 110.2. The first layer 110.1 and the second layer 110.2 are transparent and flexible and made of a suitable material such as polydimethylsiloxane (PDMS). In embodiments, the optical waveguide 110 is transparent and planar. In embodiments, the optical waveguide 110 may include additional layers (not illustrated) which may also be transparent and flexible and made of a suitable material such as PDMS. In embodiments, at least one layer of the optical waveguide 110 is transparent to visible light. In embodiments, at least one layer of the optical waveguide 110 is transparent to the light generated by the light source 120. In embodiments, the optical waveguide 110 may include only a first layer 110.1. The optical waveguide 110 may be in a planar shape such as a sheet like shape or an oval, or a suitable shape for pressing against tissue 140 to display an object 150. In embodiments, the optical waveguide 110 may be in a polygonal shape with three or more sides. In embodiments, the optical waveguide 110 may be in a disk shape. The optical waveguide 110 may be configured so that light 192 that is directed into the optical waveguide 110 under a critical angle is trapped in the optical waveguide 110 by total internal reflection. In total internal reflection the light 192 that is directed into the optical waveguide 110 remains trapped in the optical waveguide 110. For example, light 194.1 reflects off the optical waveguide 110 and the light 194.2 remains inside the optical waveguide 110. The optical waveguide 110 is configured so that when the tactile sensor 100 is pressed against a material such as tissue 140, layers 110.1 and 110.2 may deform, which causes the light 196 to scatter out of the optical waveguide 110 and strike the light sensor 130. The light in the optical waveguide 110 may stay in the optical waveguide 110 by total internal reflection until the optical waveguide 110 touches tissue 140.

The first layer 110.1 may be more flexible than the second layer 110.2 so that the first layer 110.1 may deform when the second layer 110.2 has not deformed since it is less flexible.

A layer of the optical waveguide 110 responds to a range of force from being pressed against the tissue 140 by permitting different amounts of light 194 to leave the layer 110.1 and 110.2 based on how much the layer 110.1 and 110.2 is deformed by the force. When a layer 110.1 and 110.2 is deformed a little bit, then a little bit of light 194 leaves the layer and strikes the light sensor 130. As the layer becomes more and more deformed from the force more and more light 194 leaves the layer 110.1 and 110.2 and strikes the light sensor 130. At some point, additional force continues to deform the layer 110.1 and 110.2, but the deformation does not permit additional light to leave the layer 110.1 and 110.2.

A two or more layer optical waveguide 110 provides the advantage that the optical waveguide 110 can be sensitive to a wider range of force than a single layer optical waveguide, because the first layer 110.1 of the two or more layer optical waveguide 110 can be manufactured to be more flexible than the single layer optical waveguide and the second layer 110.2 of the two or more layer optical waveguide 110 can be manufactured to be less flexible than the single layer optical waveguide; thus, providing a sensitivity to a wider range of forces.

In embodiments, the optical waveguide 110 is approximately the size of a human finger tip (20 mm×30 mm). The waveguide 110 shape and size may vary according to the application. For example, in embodiments, a large 20 cm by 20 cm waveguide may be used for breast cancer screening. In embodiments, the waveguide 110 is from 2 millimeters to 3 centimeters wide by a similar sized length. In embodiments, the waveguide is larger than the object. In embodiments, the waveguide 110 is from 2 millimeters to 50 centimeters wide by a similar sized length. In embodiments, the optical waveguide is composed of PDMS having a chemical formula of $CH_3[Si(CH_3)_2O]_nSi(CH_3)_3$, which is a high performance silicone elastomer. In embodiments, the hydroxyl-terminated PDMS RTV6186™ may be used, which is manufactured by R.S. Hughes™, Baltimore, Md. For the optical waveguide, PDMS may be produced through a process of pouring viscous fluid silicone and a catalyst into a mold cavity. The viscous fluid silicone used is vinyl-stopped phenylmethypolyer and the catalyst is a mixture of components, including methylhydrogen polysiloxane, dimethyl, methyvinyl siloxane and dimethylvinyl terminated. The viscous fluid silicone is hardened by the catalyst. The hardness or flexibility is dependent on the ratio of silicone and catalyst. The manufacture of the optical waveguide 110 is discussed further below.

In embodiments, the scattered light 196 is focused by a lens 135 and then strikes the light sensor 130.

The rigid layer 115 provides a back for the optical waveguide 110 so that when the optical waveguide 110 is pressed against an object, the optical waveguide 110 then presses against the rigid layer 115. The rigid layer 115 may be transparent to the light scattered out of the waveguide 110, which was generated by the light source 120. The rigid layer 115 may be made of a suitable material such as glass or clear plastic, which in embodiments may be heat resistant. In embodiments, the rigid layer 115 may be combined with the light sensor 130.

The light source 120 may be a light-emitting diode (LED). The light source 120 emits light into the optical waveguide 110. The light source 120 may be coupled to the optical waveguide 110 by direct coupling, prism coupling, grating coupling, or tapered coupling. In embodiments there are multiple light sources 120 that may be coupled to the waveguide 110 in different places of the waveguide 110. The light source 120 may have a spatial radiation pattern with an angle that defines the angle in which the light source 120 emits light 192. In an embodiment, the spatial radiation pattern angle is about 146 degrees about a line running through the waveguide 110. The spatial radiation pattern is discussed further below.

The light sensor 130 may be a charged-coupled device (CCD), photodetectors, or a complementary metal-oxide-semiconductor (CMOS) imager such as is commonly used in digital camera. The light sensor 130 generates signals, for example, electrical signals, to indicate an intensity of scattered light 196 that strikes pixels of the light sensor 130. The light sensor 130 may comprise a two dimensional pattern of pixels where each pixel has an intensity that indicates the intensity of light 196 that is striking the light sensor 130 at that pixel. For example, the light sensor 130 may comprise 1392×1042 pixels, each pixel having a value indicating the intensity of light 196 striking the pixel. In embodiments, the light sensor 130 may generate about 80 frames per second of the intensity of light 196 striking each of the pixels of the light sensor 130.

Lens 135 takes the light 196 and focuses the light 198 onto the light sensor 130. The lenses 135 may be formed of a suitable shape for focusing the light 198 onto the light sensor 130. The lens 135 may be a suitable material such as glass or plastic.

Tissue 140 may be any tissue such as a human breast or prostate, that may contain an object 150, which in this case is a subsurface inclusion. Tissue 140 may also be any mammary tissue that contains an object 150, which in this case is a mammary tumor. In embodiments, the tissue 140 may be material such as a plastic.

The object 150 may be a subsurface inclusion such as a tumor or a lump. The object 150 has properties such as elasticity, Young's modulus, shear modulus, shape, diameter, size, mobility, and depth (for subsurface inclusions) that may be helpful in determining whether the tumor or lump needs to be medically tested or treated.

The controller 160 may be a general purpose computer with a memory (not illustrated). The controller 160 may display an image 180 of the object 150 on the display 170 based on the electrical signals from the light sensor 130. The controller 160 is in communication with the light sensor 130 via communication link 165.1. In embodiments, the controller 160 is part of the tactile sensor 100. In embodiments, the control 160 is part of a general purpose computer or special purpose computer in communication with the tactile sensor 100 over communication link 165.1. The controller 160 may display the object 150 on the display 170 as an image 180 in the form of a gray scale image, a color visualization, a two or three dimensional reconstruction, or other suitable image 180 for viewing. The controller 160 may determine properties of the object 150 such as its elasticity, Young's modulus, shear modulus, shape, diameter, size, and depth (for subsurface inclusions). The controller 160 may display the determined properties. The controller 160 is discussed in more detail below. In embodiments, the controller 160 is remotely located so that the signals generated by the light sensor 130 may be transmitted across the Internet.

The display 170 may be a suitable display such as a liquid crystal display (LCD) or light emitting diode (LED). The display 170 takes a signal from the controller 160 and displays the information in the signal. The display 170 may be black and white or color. The display 170 is in communication with the controller 160 via communication link 165.2.

Communication links 165 may be wires or wireless communication links. As illustrated in FIG. 1, 165.1 and 165.2 are wires made of a suitable material for transmitting electrical signals such as copper.

In operation, the light source 120 emits light 190 into the optical waveguide 110. Some of the light 190 goes into the optical waveguide 110 and is trapped by total internal reflection so the light 194 propagates down the optical waveguide 110. For example, light 194.1 reflects off optical waveguide 110 as light 194.2 and does not exit out of the optical waveguide 110. Whether light 194.1 reflects off a surface or refracts (is bent) and passes through a surface is dependent on the refractive property of the optical waveguide 110 and the refractive property of the material into which the light would refract or bend (the tissue 140 or air as illustrated in FIG. 1). When the optical waveguide 110 is not being pressed against tissue 140, the light 194 is not substantially scattered out of the optical waveguide 110. When the optical waveguide 110 is pressed against tissue 140 (or another suitable substance) the light 194 that is trapped in the optical waveguide 110 is scattered and 196 strikes the light sensor 130. As illustrated in FIG. 1, the first layer 110.1 and the second layer 110.2 are deformed so that the light 196 is scattered. The more the layer 110.2 is deformed, the more light is scattered, and the greater the intensity of light 196 that will strike the corresponding part of the light sensor 130. The scattered light 196 passes through lenses 135 and is focused on the light sensor 130. The light sensor 130 generates a signal based on the intensity of light striking each part of the light sensor 130. The controller 130 takes the signal from the light sensor 130 and generates an image 180 of the object 150, and displays the image 180 on the display 170. The controller 160 may determine properties of the object 150 such as its elasticity, Young's modulus, shear modulus, shape, diameter, size, mobility, and depth (for subsurface inclusions) elasticity. As discussed below, the controller 160 may determine the centroid of the object 150 based on the intensity of light 196 that strikes the light sensor 130, and the controller 160 may determine the amount of force that is being applied to the object 150 based on the intensity of light 196 that strikes the light sensor 130.

Figure 2:
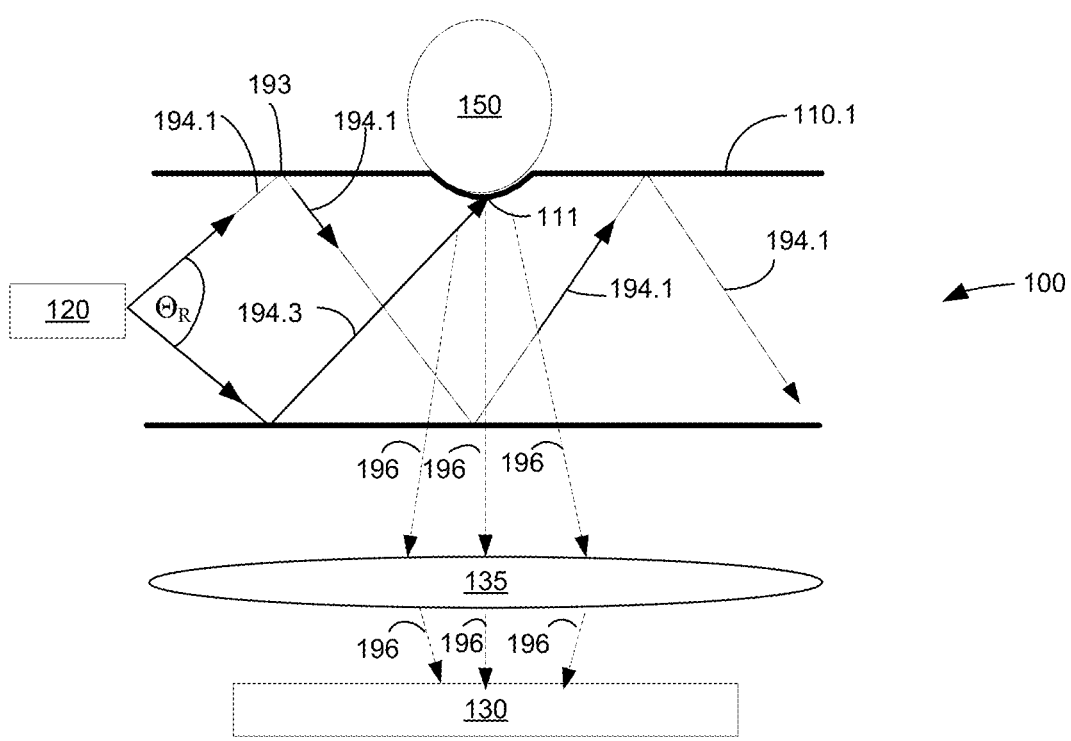
FIG. 2 illustrates an embodiment of the tactile sensor where light is being scattered because the tactile sensor is being pressed against an object.

FIG. 2 illustrates an embodiment of the tactile sensor where light is being scattered because the tactile sensor is being pressed against an object. The light source 120 emits light 194 into the first layer 110.1 of the optical waveguide 110. In the embodiment illustrated in FIG. 2, there is only one flexible transparent layer 110.1. The light source 120 emits light 194 with a spatial radiation patter having an angle $\Theta_R$. $\Theta_R$ is chosen so that the light 194 that is emitted by the light source 120 enters the first layer 110.1 and is trapped in the first layer 110.1 by total internal reflection. For example, light 194.1 is emitted by the light source 120 and enters into the first layer 110.1. The light 194.1 strikes the edge of the first layer 110.1 at 193. The light 194.1 reflects back into the first layer 110.1 because of the refractive properties of the first layer 110.1, and the refractive properties where the light 194.1 would have gone if it had gone through the edge of the first layer 110.1. Light 194.1 then continues to propagate down the first layer 110.1.

FIG. 2 is a side view of the tactile sensor 100. The tactile sensor 100 is pressed into an object 150 in FIG. 2. Because the first layer 110.1 is flexible, an edge of the first layer 110.1 deforms in at 111. Light 194.3 strikes where the first layer 110.1 is deformed at 111 and diffuses. The total internal reflection light 194.3 becomes scattered light 196. This occurs because the angle where the light 194.3 hits the edge of the first layer 110.1 changes. The scattered light 196 then passes through the lens 135 and is focused on the light sensor 130. The light sensor 130 generates signals from the light 196. Information regarding the object 150 is then determined by the controller (not illustrated) based on the signals.

In an embodiment, the optical waveguide 110 of the tactile sensor 100 comprises three flexible transparent layers. In an embodiment the optical waveguide is planar and in the approximate shape of a sheet In an embodiment the first layer, the second layer, and the third layer are made of PDMS.

Figure 3A:
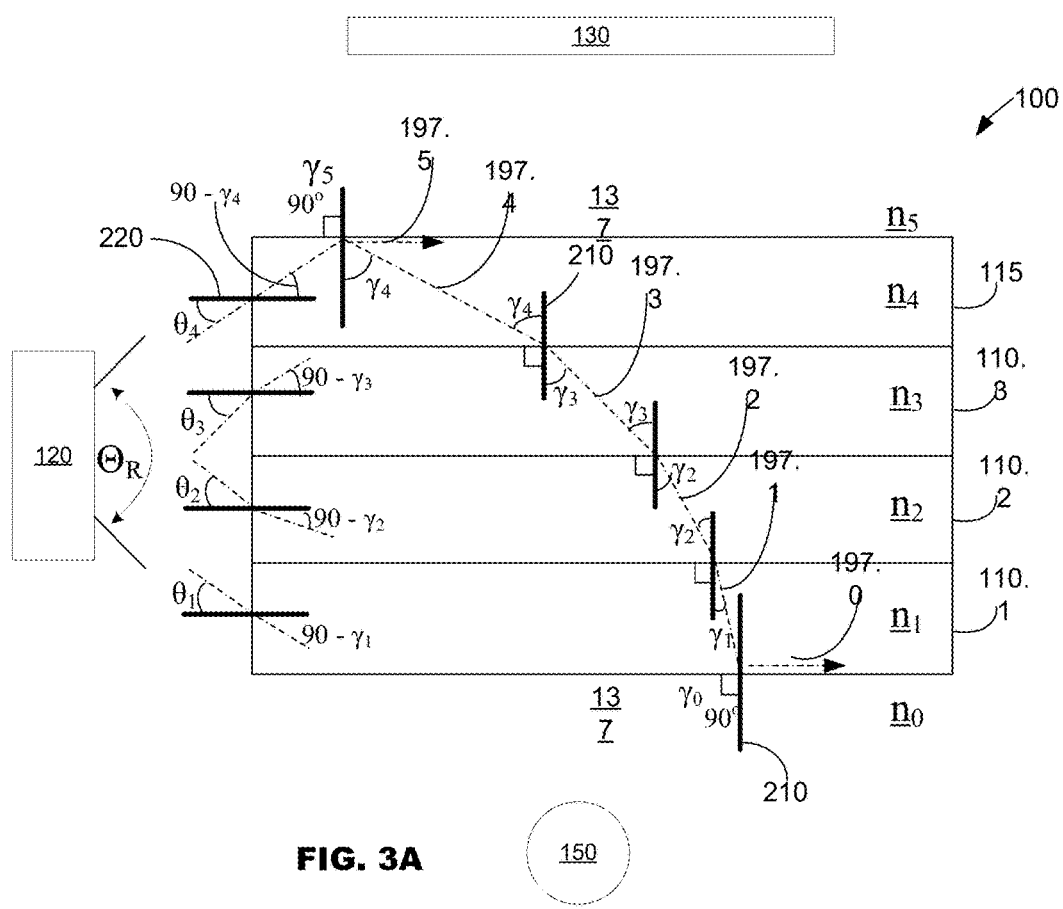
FIG. 3A is an illustration of an embodiment of a optical waveguide.

FIG. 3A is an illustration of an embodiment of an optical waveguide. Illustrated in FIG. 3A is a rigid layer 115, air 137, and an object 150 into which the optical waveguide 110 may be pressed. Also shown in FIG. 3A is a light source 120, a light sensor 130, and an optical waveguide 110 which includes a first layer 110.1, a second layer 110.2, and a third layer 110.3. Also illustrated is light 197 propagating through the optical waveguide 110. The light 197 refracts or bends as it passes from one substance to the next because of differences in the refractive indexes of the substances $n_0$, $n_1$, $n_2$, $n_3$, $n_4$, and $n_5$. Additionally, $\Theta_R$ the spatial radiation patter of the light source 120 is illustrated. The optical waveguide 110 is transparent and flexible and is planar in the approximate shape of a sheet.

Light is emitted into the optical waveguide 110 from the light source 120. In embodiments, it is advantageous for the light 197 to stay in the optical waveguide 110 by total internal reflection until the light is scattered out of the optical waveguide 110 by the deforming of the optical waveguide 110 from being pressed against an object 150.

Some light that is generated by the light source 120 may not be captured by total internal reflection. For example, there may be impurities in the waveguide that cause the light to scatter out of the waveguide rather than reflect back into the waveguide. This light may be called noise light, which is light that refracts out of the optical waveguide 110 not because of the deformation of the optical waveguide 110 from the pressing the waveguide against an object 150, but rather for other reasons.

The noise light may cause several problems. For example, the noise light may strike the light sensor 130 (see FIG. 1) and generate signals, which creates noise in the generated signals. Additionally, noise light may make it more difficult to emit enough light into the optical waveguide 110 from the light source 120 so that there is enough light in the optical waveguide 110 to be scattered into the light sensor 130 when the optical waveguide 110 is pressed against an object 150.

Each of the materials in FIG. 3A has a property called the "refractive index", denoted $n_0$, $n_5$, for air 137, $n_1$ for the first layer 110.1, $n_2$ for the second layer 110.2, $n_3$ for the third layer 110.3, and $n_4$ for the rigid layer 115. As light 197 passes from one medium to another as for example from the air 137 to first layer 110.1, the result is a bending of light 197 at an angle.

Materials may be manufactured to have selected refractive indices. In the embodiment illustrated in FIG. 3A, the following values were selected: $n_1=1.41$, for the first layer 110.1, $n_2=1.40$ for the second layer 110.2, $n_3=1.39$ for the third layer 110.3, and $n_4=1.38$ for the rigid layer 115. For air 137, $n_0$, $n_5$, are approximated at 1.0. With these values for refractive indexes of the optical waveguide 110 and the rigid layer 115, embodiments set $\Theta_R$, the spatial radiation pattern of the light source 120, to 143.96 degrees, so that the light emitted into the waveguide 110 from the light source 120 remains substantially in the optical waveguide 110 (and the rigid layer 115) by total internal reflection. In this embodiment, the light illuminates the waveguide so that total internal reflection occurs.

By substantially in the optical waveguide 110 it is meant that the noise light as described above does not generate so much noise at the light sensor 130 as to prevent generating an image of the object 150, and that the noise light is not so great as to prevent enough light to be captured by total internal reflection so that light will be scattered out of the waveguide 110 by the deformation of the waveguide 110 from pressing the waveguide 110 against the object 150.

The values for the refractive indexes: $n_0$, $n_1$, $n_2$, $n_3$, $n_4$, and $n_5$ and $\Theta_R$ may be determined as follows.

Snell's law as described in Equation (1) below determines how much the light bends when the light travels from one material to another.

$$\text{Snell's Law is } n_1/n_2 = \sin y_2 / \sin y_1. \quad \text{Equation (1):}$$

For example, when light 197.3 passes from $n_3$ to $n_4$ as light 197.4, Snell's Law can be used to determine the angle $\gamma_4$ from $\gamma_3$ and the refractive indexes $n_4=1.38$ and $n_3=1.39$ as used in this embodiment. Snell's Law gives: $(1.38/1.39) = (\sin \gamma_3/\sin \gamma_4)$, which may be used to derive: $\gamma_4 = \sin^{-1}[(1.39/1.38)*\sin(\gamma_3)]$. The angles $\gamma_3$ and $\gamma_4$ are measured from the normal 210 which is a line ninety (90) degrees from the surface of the optical waveguide 110. When light 197.3 goes from $n_3$ to $n_4$, the light 197.4 is bent so that the angle $\gamma_4$ is greater than the angle $\gamma_3$; or, the light 197.4 is bent away from the normal 210 and more along the axis of the rigid layer 115. The opposite occurs when the light 197.4 travels from the rigid layer 115 to the third layer 110.3.

The critical angle $\theta_C$ which determines whether or not light will reflect off a boundary between two different materials is given by the following equation.

$$\theta_c = \sin^{-1}(n_2/n_1). \quad \text{Equation (2):}$$

The refractive index of air 137 is approximately one so having the refractive index of the optical waveguide 110 being larger than one will enable light to be captured by total internal reflection, since by Equation (2) total internal reflection is not possible when the refractive index of a material is less than the surrounding material. With refractive indexes of $n_1=1.41$, $n_2=1.40$, $n_3=1.39$ $n_4=1.38$, and with a refractive index of air $n_0$, $n_5=1$, it is not possible to have total internal reflection of light within only one of the layers except the first layer 110.1 (as to have total internal reflection the refractive index has to be lower on both sides.)

Equation (1), Snell's Law, can be used to express a relationship with the propagation angles in each layer of the optical waveguide 110 and the rigid layer 115.

Since light 197 must obey Snell's Law in propagating though the optical waveguide 110, the following equations must be met.

$$n_1 * \sin \gamma_1 = n_0 * \sin \gamma_0. \quad \text{Equation (3):}$$

$$n_2 * \sin \gamma_2 = n_1 * \sin \gamma_1. \quad \text{Equation (4):}$$

$$n_3 * \sin \gamma_3 = n_2 * \sin \gamma_2. \quad \text{Equation (5):}$$

$$n_4 * \sin \gamma_4 = n_3 * \sin \gamma_3. \quad \text{Equation (6):}$$

$$n_5 * \sin \gamma_5 = n_4 * \sin \gamma_4. \quad \text{Equation (7):}$$

If $\gamma_0$ and $\gamma_5$ are set to ninety (90) degrees, then the light 197 for the entire optical waveguide 110 and the rigid layer 115 will have total internal reflection. Note that an angle of ninety (90) degrees means the light 197 is traveling along the axis of a layer of the optical waveguide 110 as angles are measured relative to the normal 210. So light 197 traveling at an angle greater than $\gamma_i$ (a higher angle is more parallel with the waveguide) in the respective layer of the optical waveguide will be trapped by total internal reflection in the optical waveguide 110 and rigid layer 115 as a whole.

The acceptance angles $\theta_1$, $\theta_2$, $\theta_3$, and $\theta_4$, are the maximum angles at which light 197 may be directed into the corresponding layer of the optical waveguide 110 and for the light 197 to be trapped in the optical waveguide 110 by total internal reflection. The acceptance angles are measured along an axis 220 of the optical waveguide 110, so $\theta_i$=ninety (90)$-\gamma_i$. Using Snell's Law, Equation (8) can be derived.

$$\sin\theta_i = n_i * \sin(90-\gamma_i) = n_i * \cos(\gamma_i). \qquad \text{Equation (8):}$$

Further transforming Equation (8) using geometric relationships and algebra gives:

$$\sin\theta_i = n_i * \cos(\gamma_i) = n_i * (1-\sin^2\gamma_i)^{1/2} = ((n_i)^2 - (n_i)^2 * \sin^2\gamma_i))^{1/2}. \qquad \text{Equation (9):}$$

Additionally, since all $n_i * \sin(\gamma_i) = n_0$ in Equations (3)-(7), for $n_0=1$ for air, using algebra and geometry gives the following:

$$\theta_i = \sin^{-1}[(n_i)^2 - 1)^{1/2}]. \qquad \text{Equation (10):}$$

This means that light incident on layer n; under the acceptance angle $\theta_i$ will be trapped by total internal reflection inside the optical waveguide 110 and the rigid layer 115. For $n_1=1.41$, $n_2=1.40$, $n_3=1.39$, and $n_4=1.38$, the value for the acceptance angles are: $\theta_1=83.73$ degrees, $\theta_2=78.46$, $\theta_3=74.89$ degrees, and $\theta_4=71.98$ degrees. If the lowest acceptance angle is used for $\Theta_R$ the spatial radiation pattern of the light source 120, then $\Theta_R$ is set to (2*71.98) 143.96 degrees. The light emitted into the waveguide 110 from the light source 120 will remain substantially in the optical waveguide 110 (and the rigid layer 115) by total internal reflection.

Additionally, in the embodiment illustrated in FIG. 3A, the flexibility or elastic modulus of the layers of the optical waveguide 110 were selected as $n_1=1.4\times10^5$ Pa., $n_2=8.0\times10^4$ Pa., and $n_3=3.4\times10^4$ Pa.

Figure 3B:
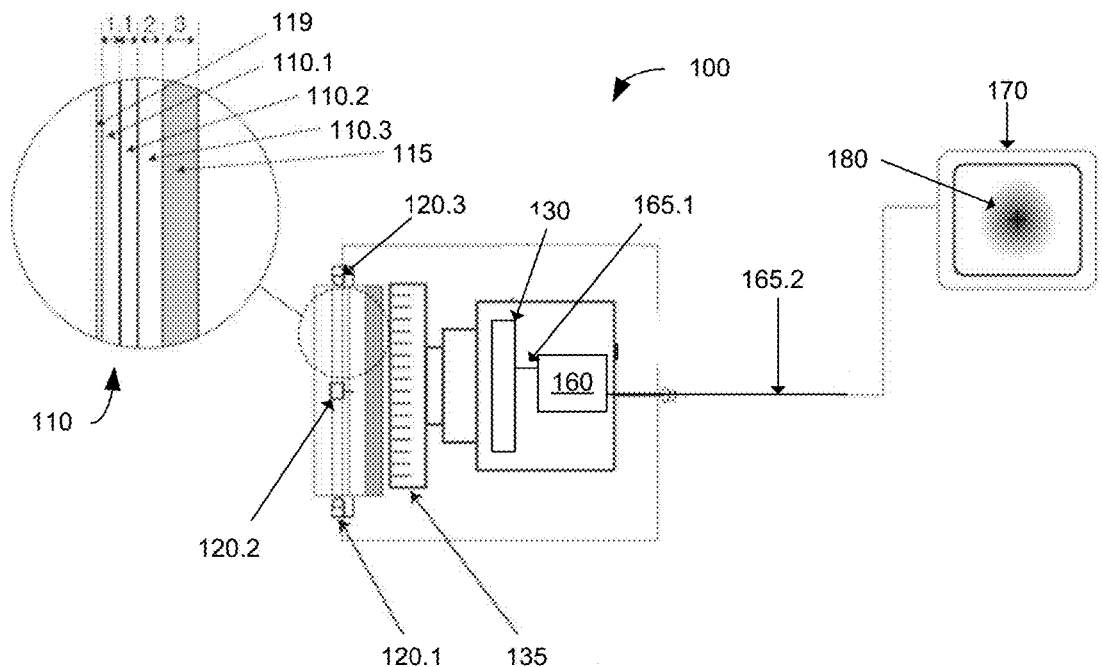
FIG. 3B illustrates an embodiment of the tactile sensor.

FIG. 3B illustrates an embodiment of the tactile sensor 100, which includes an optical waveguide 110, light sources 120.1, 120.2 (not illustrated), and 120.3, light sensor 130, lens 135, and rigid layer 115. The embodiment illustrated in FIG. 3B may be manufactured from a digital camera.

In the embodiment of the optical waveguide 110, there is a first layer 110.1, a second layer 110.2, and a third layer 110.3. The optical waveguide 110 comprises a membrane 119 for protection. The optical waveguide 110 is backed by a rigid layer 115, which provides a backing for when the tactile sensor 100 is pressed against an object 150 (not illustrated in FIG. 3B).

In the embodiment in FIG. 3B, the height of the first layer 110.1 is 1 mm, the height of the second layer 110.2 is 3 mm, and the height of the third layer 110.3 is 5 mm. The elastic modulus of the first layer (outer layer) 110.1 is $1.4\times10^5$ Pa, the elastic modulus of the second layer 110.2 is $8.0\times10^4$ Pa, and the elastic module of the third layer 110.3 is $3.4\times10^4$ Pa. The selection of the elastic moduli and the height of each layer is similar to human skin. The rigid layer 115 is similar to a finger bone or finger nail for providing a backing for other layers of the optical waveguide 110. Having multiple layers with different modulus values allows for greater sensitivity and for a wider range of measurements as a layer 110.1, 110.2, 110.3 will not significantly contribute to the amount of scattered light until the layer 110.1, 110.2, 110.3 is deformed from being pressed against the object. An optical sensor 100 comprising an optical waveguide with only one layer having the same elastic modulus of the first layer 110.1 illustrated in FIG. 3B, has the following disadvantage. Most of the light is scattered out of the optical waveguide 110 at a force that is smaller than a force that deforms the third layer 110.3 of the optical waveguide 110 of FIG. 3B, so a single layer design may not be sensitive across as wide a range of force values as a multi-layered waveguide design. Additionally, the embodiment illustrated in FIG. 3B has been shown experimentally to be sensitive and accurate.

The illustrated embodiment optical waveguide 110 has a force sensitivity of approximately $2.5\times10^{-3}$ Newtons compared to the average fingertip force sensitivity of approximately $2\times10^{-2}$ Newtons. As illustrated below, the tactile sensor 100 has the advantage over conventional tactile sensors, such as those that rely on piezoelectric force sensors, in that the force applied to an object can be determined by the scattered light so that separate force sensors are not required.

The membrane 119 is flexible and transparent and may have a height of less than 1 mm. The membrane 119 may be replaceable and may be replaced for hygienic reasons. The membrane 119 may be manufactured to have a refractive index to facilitate total internal reflection of light in the optical waveguide 110 as described with regards to FIG. 2.

The light sources 120.1, 120.2, 120.3, and 120.4 (not illustrated) may comprise light-emitting diodes (LEDs) coupled to the four edges of the planar optical waveguide 110. Light source 120.4 is located on the opposite side of the tactile sensor 100 from light source 120.2. The LEDs may be micro LEDs such as LEDs from Unique-Leds™ of Newalla, Okla. Each of the LEDs may be coupled to the optical waveguide 110 by direct coupling, prism coupling, grating coupling, or tapered coupling. Coupling efficiency is determined by how much of the light is emitted into the optical waveguide 110 that will be captured by total internal reflection. In embodiments, the LEDs 120 are coupled to the optical waveguide 110 with a piano-convex lens from Newport Corporation™ of Irvine, Calif. The piano-convex lens may be, for example, 12.7 mm in diameter with a focal distance of 12.7 mm. The direction and incident angle of light may be calibrated to increase the efficiency. The LEDs may have a spatial radiation pattern $\Theta_R$ set to 143.96 degrees or a suitable spatial radiation pattern $\Theta_R$ as described above for emitting light into the optical waveguide 110 so that substantially all the light is captured by total internal reflection.

The light sensor 130 may be a CMOS with 4.65 µm×4.65 µm individual pixel size, which can be purchased from FLEA2 Point Grey Research™ of British Columbia, Guppy™ from Allied Vision Technologies™ of Germany, and from other sources. In embodiments, the light sensor 130 may be a CMOS with 8.4 µm×9.8 µm individual pixel size, which can be purchased from AVT Guppy™ camera of Germany. The light sensor 130 may generate 80 pictures or frames per second of the light intensity information. The spatial resolution of the fingertip is at least 0.1 mm. The size of a fingertip is approximately 20 mm×30 mm. So, the number of sensors for the fingertip may be approximately 200×300. In embodiments, the spatial resolution of the light sensor 130 is 4.65 µm with approximately 4301×6415 pixels in a grid on the same area as a fingertip (20 mm×30 mm.) In embodiments, the spatial resolution of the light sensor 130 is 9.8 µm with approximately 2041×3061 pixels in a grid on the same area as a fingertip (20 mm×30 mm.) Each pixel of the light sensor 130 may have a value indicating the intensity of light that strikes the pixel. The value indicating the intensity may be represent by an eight (8) bit number so that values may range from zero (0) to two-hundred-and-fifty-five (255). In embodiments, the value indicating the intensity may be represented by numbers with more bits.

In the illustrated embodiment, the lens 135 gives a resolution of 1392 µm (H)×1042 µm (V) with a 60 degree view angle. In embodiments, the lens 135 gives a resolution of 6451 µm (H)×4821 µm (V) with a 60 degree view angle. The rigid member 115 may be a heat-resistant borosilicate glass plate. In embodiments, a camera may be used for the light sensor 130, the lens 135, the controller 160, and/or the display 170.

Figure 3C:
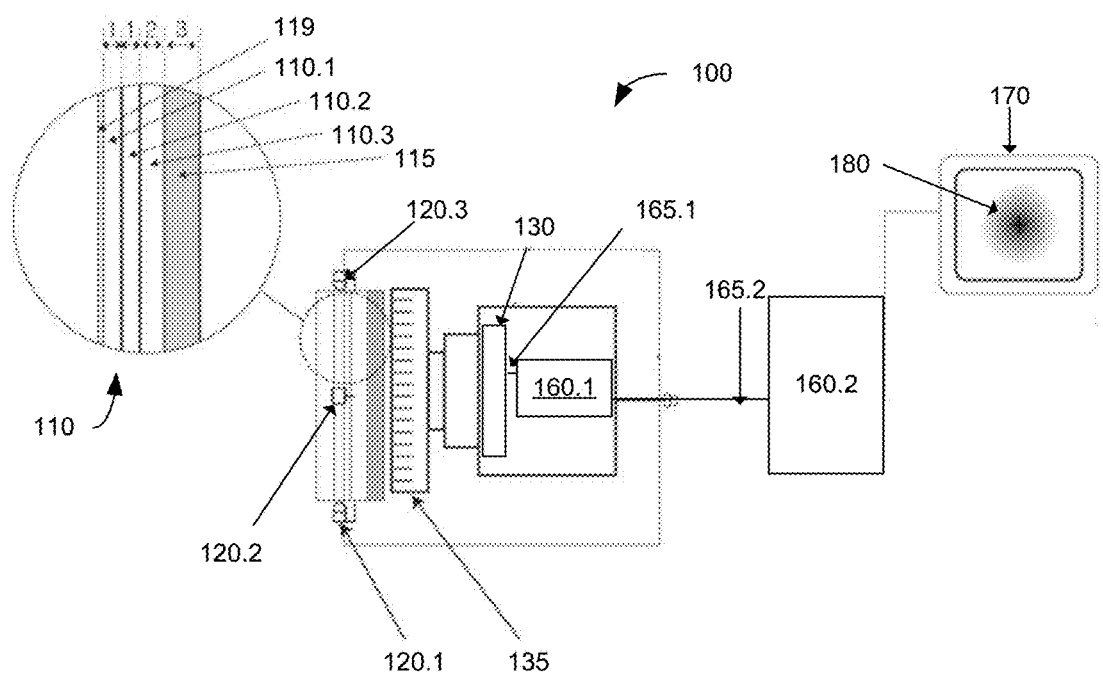
FIG. 3C illustrates an embodiment of the tactile sensor.

FIG. 3C illustrates an embodiment of the tactile sensor 100 with two controllers 160.1 and 160.2. Controller 160.2 may be a general purpose computer such as laptop or desktop computer. Software for carrying out the methods described herein may be loaded on the controller 160.2. The tactile sensor 100 may send signals to controller 160.2 that may be raw signals from the light sensor 130, or the signals may have processing done to them prior to sending the signals to the controller 160.2 For example, the tactile sensor 100 may be configured to generate grey scale and color images of the objects, but not configured to calculate the elasticity of the object as described above. Controller 160.1 is optional. In an embodiment, controller 160.1 performs simple signal processing to send the signals generated from the light sensor 130 to the controller 160.2 via a cable 165.2 which may be a USB cable. The controller 160.2 may be a general purpose computer and may process the signals and generate images of the object and calculate properties of the object such as size, shape, and elasticity.

Figure 4A:
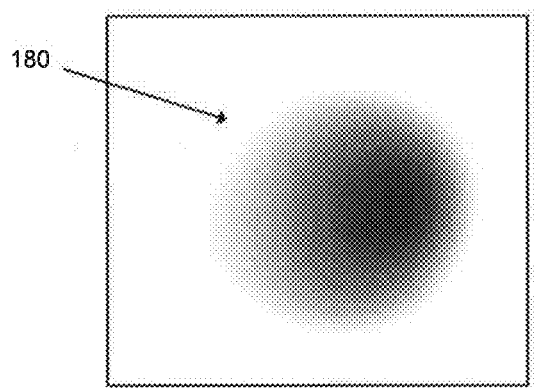
FIGS. 4A, 4B, and 4C illustrate images generated by the controller.
Figure 4B:
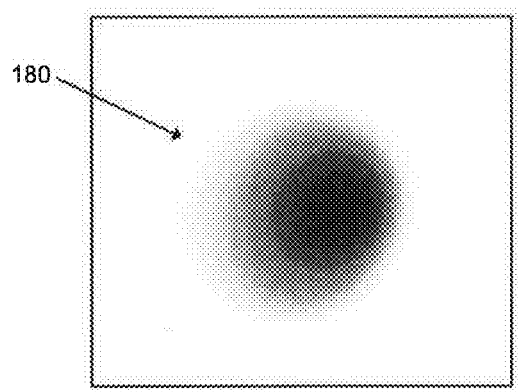
Figure 4C:
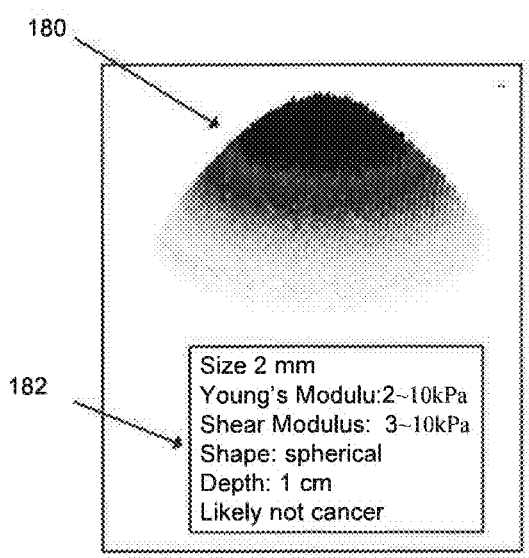

FIGS. 4A, 4B, and 4C illustrate images generated by the controller. The controller takes the signals generated by the light sensor and generates an image 180, and displays the image 180 on the display. The images 180 are of a sample tactile spherical object made with diameter of 2 mm under 0.7 Newtons of force applied on a normal of the object. FIG. 4A is a grey scale image. FIG. 4B is a grey scale reproduction of a color image where the controller takes the grey scale image and replaces ranges of grey scale values with colors. FIG. 4C is a three dimensional image of the object. The controller generated the image using a "shape from shading method" known in the art of image processing. In embodiments, the controller may generate a two-dimensional image or a three-dimensional image. In embodiments, the controller may generate an image that is false colored according to a calculated property of the object such as elasticity. In embodiments, the colors may represent the pressure or force applied to the tactile sensor. In embodiments, the controller may also display properties 182 of the object such as the size, shape, diameter, mobility, depth, shear modulus, Young's Modulus, and a diagnoses of whether or not the object is malignant or benign. In embodiments, the controller may determine a shape of the object based on the shape of the pixels that are struck by the scattered light and the intensity of the scattered light in each of the pixels. The controller may determine that pixels with a greater light intensity of scattered light indicate that a greater force has been applied to the corresponding portions of the optical waveguide, which may indicate that the corresponding portions of the optical waveguide are closer to the object.

Figure 5A:
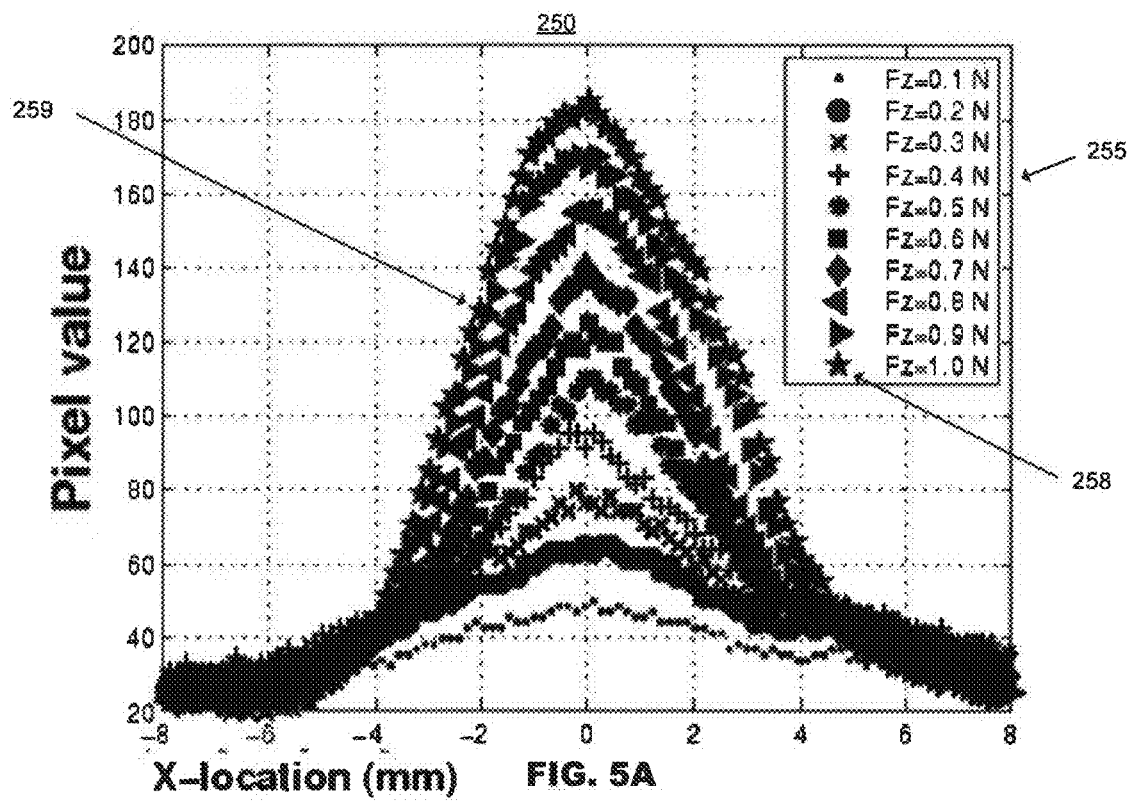
FIG. 5A illustrates a graph of light intensity value vs. location from a centroid of an object sensed by the tactile sensor for different sizes of applied force.

FIG. 5A illustrates a graph of light intensity value vs. location from a centroid of an object sensed by the tactile sensor for different sizes of applied force.

Graph 250 in FIG. 5A was generated by using a loading machine with a force gauge to measure the applied force to an embodiment of the optical waveguide. Legend 255 illustrates which symbol in the graph 250 was used to plot different forces applied to the waveguide. Graph 250 is a composite graph of the different forces applied to the waveguide. For example, the star 258 was used to graph the pixel values when a force of 1.0 Newton was applied to the optical waveguide. The force gauge has a probe with a tip of 2 mm radius to measure the force from zero to fifty Newtons, with a resolution of $1.0 \times 10^3$ Newtons. The light sensor used had a range from zero to two-hundred and fifty-five per pixel to measure the light intensity. The force applied to the waveguide started with zero Newtons and increased in a stepwise fashion up to one Newtons. Pixel values are graphed for each 0.1 value of Newtons 255 from along a horizontal line passing through the centroid of where the 2 mm tip was pressed into the waveguide. For example, the star symbol 258 at location 259 represents the light intensity values for when one Newton of force was applied to the optical waveguide at a location 259 that is approximately −2 mm from where the force was applied.

The graph 250 shows a Gaussian like bell shape for light intensity values for different forces measured in Newtons applied, and the maximum value is on the centroid (0 position) of where the tip was pressed into the optical waveguide. One advantage of the tactile sensor over a fingertip is that the tactile sensor does not exhibit hysteresis.

Figure 5B:
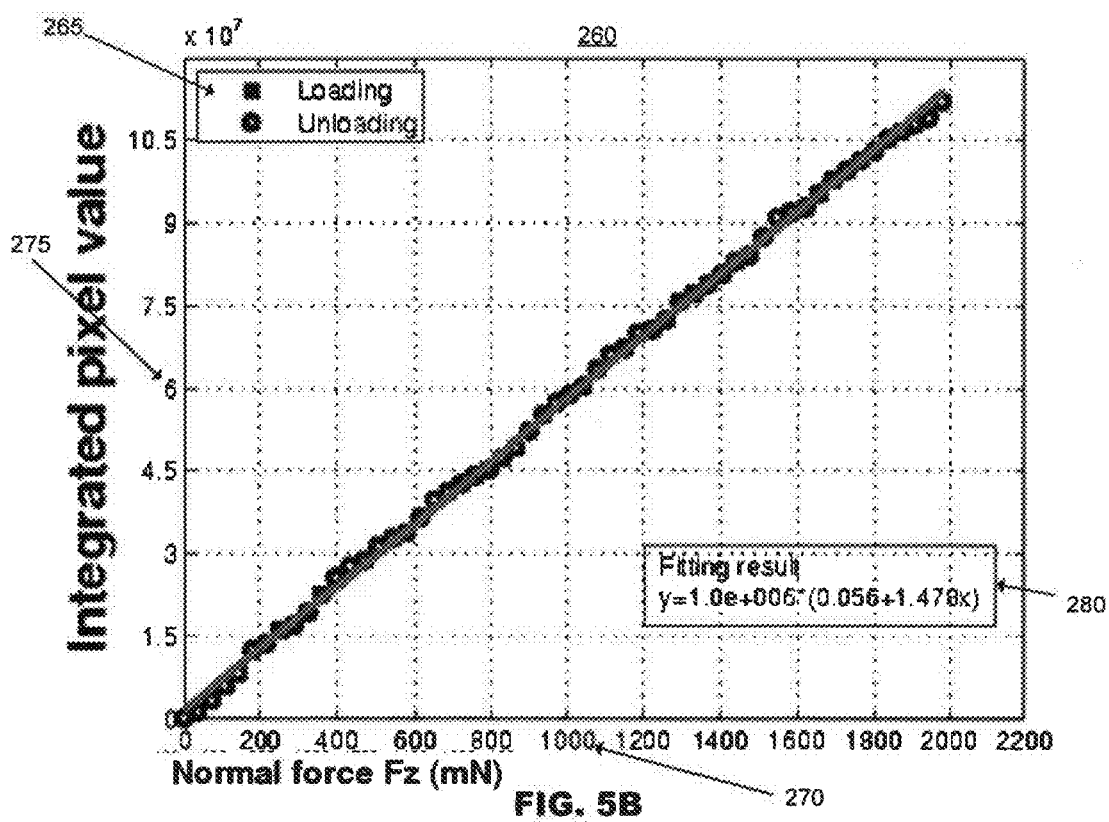
FIG. 5B illustrates the relationship between force and integrated pixel value from FIG. 5A, which may be used to calculate the strain on an object or object.

FIG. 5B illustrates the relationship between force and integrated pixel value from FIG. 5A, which may be used to calculate the strain on an object or subsurface inclusion. FIG. 5B is derived from FIG. 5A by summing the light intensity values that are generated by the light sensor from the application of force to the optical waveguide. The graph 260 includes values for when force was applied to the optical waveguide and as the force was released from the optical waveguide.

For example, when one Newton of force was applied to the optical waveguide the light sensor generated light intensity signals that are graphed in FIG. 5A with a star 258. These values were summed to give the value six 275 at one Newton of force 270.

Because the light intensity values are linear with respect to the amount of force that is applied to the optical waveguide, the controller can use the light intensity values to determine the approximate force that is applied to a object. The force applied to the optical waveguide is the same as the force applied to the tip that pressed into the optical waveguide.

The data in the graph of FIG. 5B fits the following equation:

Integrated light intensity=$1.0 \times 10^6 \times (0.056 + 1.478 *$applied force)(element 280 in FIG. 5B), where applied force is given in milli Newtons.     Equation (11):

Different embodiments of the waveguide may be tested to determine the particular relationship between applied force and integrated pixel value for each embodiment. This determination may be considered part of a calibration of a light sensor 100.

Determining the force applied to an object or subsurface inclusion may be used to generate an image of the object and may be used to determine properties of the object.

Embodiments of the controller use the approximate force applied to an object to calculate the stress on an object Embodiments of the controller use the stress to determine the elasticity of an object, which may be used to diagnose whether a subsurface inclusion is benign or malignant. The elasticity of an object is given by the following:

$$\text{Elasticity } (E) = \text{stress/strain.} \quad \text{Equation (12):}$$

The strain is a measure of how much the object is deformed. The stress is the amount of force applied to the object per unit area. Embodiments of the controller calculate the amount of stress by summing the intensity values generated by the light sensor and then approximating the force applied based on the relationship between light intensity and force as discussed above. Embodiments of the controller then estimate the area of the object the force is applied to based on the size of the pixels of the light sensor.

Accordingly, if we let I(x, y) be the individual pixel values representing the light intensity, and P(x,y) be the contact stress (force per area), then:

$$P(x,y) = g\ (I(x,y)), \text{ where g is a conversion function, since } I(x,y) \text{ and } P(x,y) \text{ must be proportional.} \quad \text{Equation (13):}$$

If C is the contact area between the optical waveguide and the touched object, then the force F is obtained by integrating the stress over the contact area as follows:

$$F = \int_C P(x, y)\, dC. \quad \text{Equation (14)}$$

Additionally, the strain then may be estimated by:

$$S = \int_C P(x, y)\, dC / C, \quad \text{Equation (15)}$$

where P is the contact stress and C is the contact area.

Thus, the controller can estimate the stress by estimating the force and estimating the area over which the force is applied.

Since the individual pixel values are discrete, in embodiments, the controller estimates the stress by using the individual pixels values to estimate the force as described above, and then estimates the area of the object that produced the scattered light for that individual pixel. In embodiments, the controller may calculate the approximate area of the object as being the same as the area of the pixel size.

Figure 6:
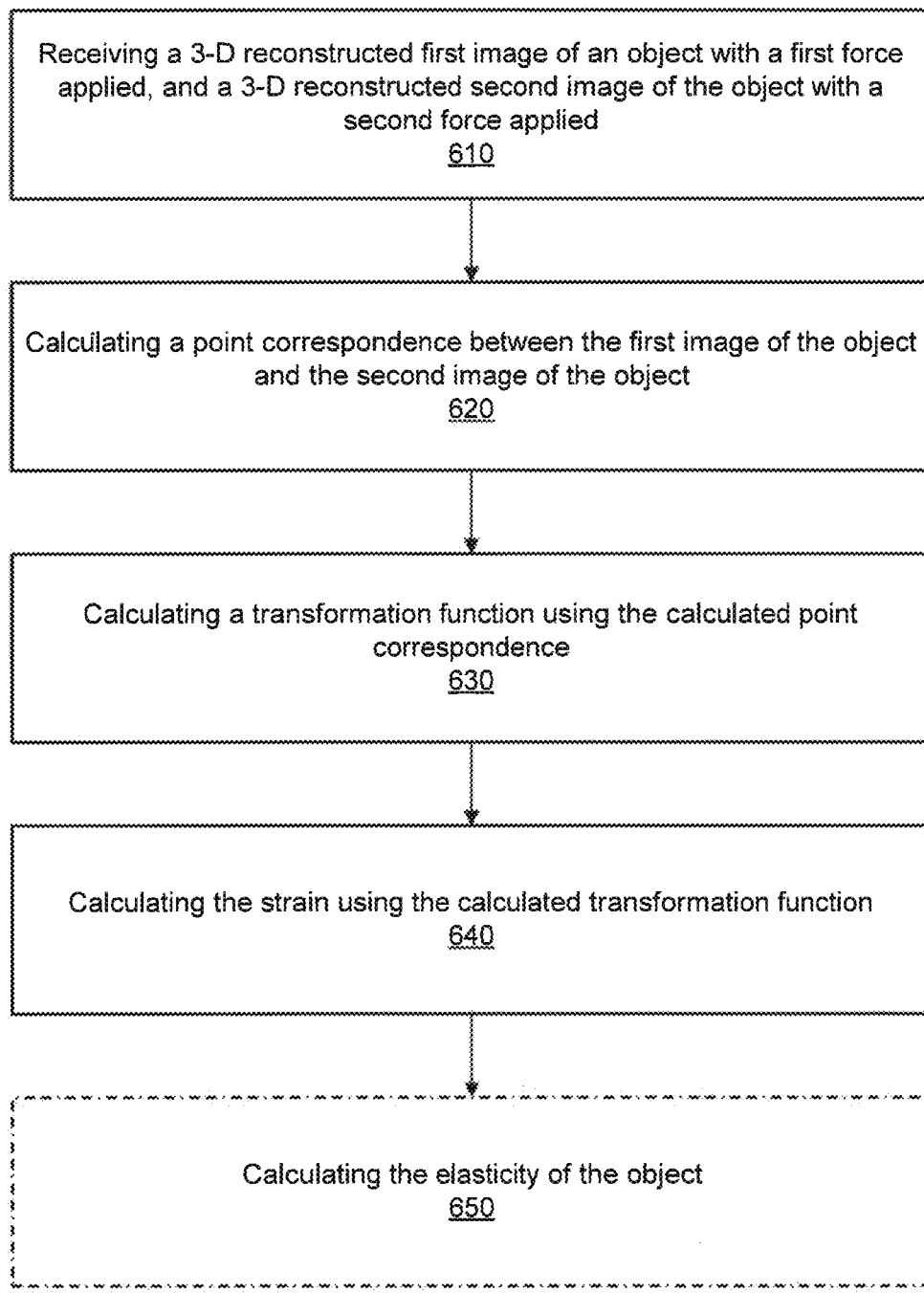
FIG. 6 illustrates a method to determine the strain of an object.

FIG. 6 illustrates a method to determine the strain of an object. Strain is the geometrical deformation measurement indicating the relative displacement between points on an object. In embodiments, the controller calculates the strain for two different forces on the same object. The following method operates by measuring the displacement by tracking the change in position of control points extracted from the first image and the second image.

Figure 7:
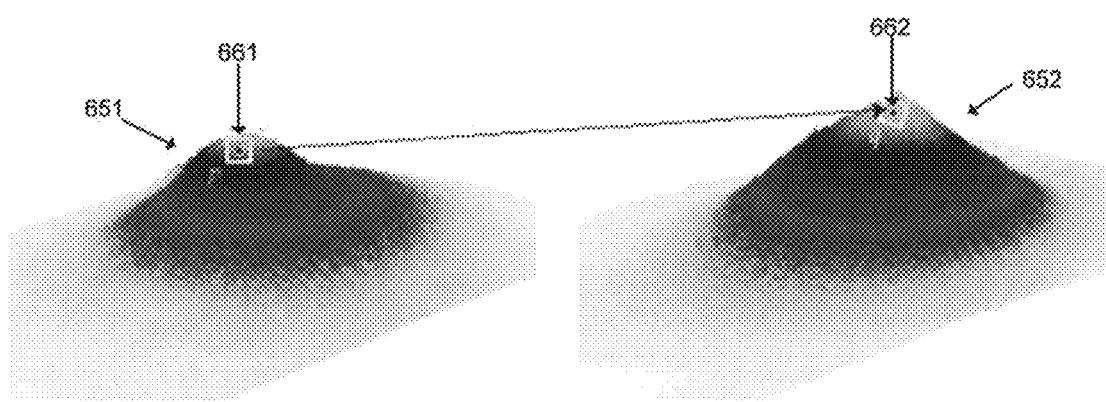
FIG. 7 illustrates a 3-D reconstructed first image and a 3-D reconstructed second image.

The method of FIG. 6 begins at 610 with receiving a 3-D reconstructed first image of an object having a first force applied, and a 3-D reconstructed second image of the object having a second force applied. In embodiments, the controller of the tactile sensor may construct a 3-D image from the signals generated from the light sensor. See the explanation with regard to FIG. 4C. FIG. 7 illustrates a 3-D reconstructed first image 651 and a 3-D reconstructed second image 652. The first image 651 and second image 652 are reconstructed 3-D images of an object that comprises a Veraflex™ CL2000X soft polymer. The first image 651 is from data gathered from an embodiment of the tactile sensor with 0.7 Newtons of force applied to the object. The second image 652 is from data gathered from an embodiment of the tactile sensor having 1.2 Newtons of force applied to the object. In embodiments, the controller may generate the 3-D reconstruction of the first image and the second image.

The method of FIG. 6 continues at 620 with calculating a point correspondence between the first image of the object and the second image of the object. FIG. 7 illustrates a point correspondence calculated by the controller between point p(x, y, z) 661 of the first image and point q (x, y, z) 662 of the second image.

Accordingly, the controller may calculate a point correspondence between the first image of the object and the second image of the object, as follows. Let $O_1$ represent the first image 651, and $O_2$ represent the second image 652. The controller then extracts a number of control points from the surface of $O_1$ and $O_2$. Let, $P = \{p_1, p_1, \ldots, p_i\}$ be a point set extracted from $O_1$ and $Q = \{q_1, q_1, \ldots, q_j\}$ be a point set extracted from $O_2$.

If the object is deformed by the tactile sensor, the distance between points on the object before and after being deformed may be far apart; however, points that are near or adjacent to a specific point before the object is deformed will not be too far from that specific point after the deformation since points near a specific point may not move too far from the specific point due to the physical constraint that the surface of the solid object remains in tact. Near or adjacent points to a point may be referred to as local adjacent points. So, the controller selects A points that are local adjacent points, denoted N, to each point $p_i$ in P, which are denoted as $N_a^{p_i}$, a=1, 2, . . . , A. The points $N_a^{p_i}$ may be selected by the controller to be in a circle centered at $p_i$.

The controller may also select points that are adjacent to each point in Q which are denoted as $N_b^{q_j}$, b=1, 2, . . . , B. The points $N_b^{q_j}$ may be selected by the controller to be in a circle centered at $q_1$. The controller may set the radius of the circles as the median value of all Euclidian distances between point pairs in P and Q.

The controller calculates a "fuzzy" correspondence matrix M. Each element of M has a continuous value between [0, 1], which indicates the correspondence weight between $p_i$ and $q_j$. An optimal match denoted $\hat{M}$ is found by maximizing the energy function denoted E(M) over all possible correspondence matrixes M, as follows.

$$\hat{M} = \operatorname*{argmax}_M E(M). \quad \text{Equation (16)}$$

Equation (17) defines how to calculate the energy function, E(M).

$$E(M) = \sum_{i=1}^{I} \sum_{b=1}^{B} \sum_{j=1}^{J} \sum_{a=1}^{A} M_{p_i, q_j} M_{N_a^{p_i}, N_a^{q_i}}, \text{ where} \quad \text{Equation (17)}$$

$$\sum_{i=1}^{I} M_{p_i, q_j} = 1, \forall\ i, \text{ and } \sum_{j=1}^{J} M_{p_i q_j} = 1, \forall\ j, \text{ and} \quad \text{Equation (18)}$$

$$M_{p_i q_j} \in [0, 1].$$

The controller assigns each point $p_i \in P$ with a set of matching probabilities using the shape context distance as disclosed in Belongie, et al. 2000. After the initial probability assignment, the controller updates the matching probabilities using the relaxation labeling process as disclosed in Sinkhorn 1964 and Pelillo, et al., 1994.

The controller will assign a matching probability that maximizes within a predetermined error amount denoted E(M) under the relaxed condition as $M_{Pi,qj} \in [0, 1]$ using a relaxation labeling process. At the end of the process, each point $p_i \in P$ will have one unambiguous matching probability.

The relaxation labeling process performed by the controller was modified as follows. A new compatibility coefficient quantifies the degree of agreement that $p_i$ matches to $q_j$ and $N_a^{pi}$ matches $N_b^{qj}$. The new compatibility coefficient is measured by the vector set from each point of the vector set to all other points of the vector set. This has the advantage that in the non-rigid degradation of point sets, a point set has usually changed its location, but the neighborhood structure of each point is well preserved due to the physical constraint of the object not deforming too much. The displacement of a point and its adjacent point constrain one another. Thus, if the distance and angle of a point pair $(p_i, N_a^{pi})$ and its corresponding point pair $(q_j, N_a^{qj})$ are similar, they are assigned a high correlation. The correlation is even higher when the points $(p_i, N_a^{pi})$ are closer to each other.

The controller calculates similarity constraints, represented as $\alpha$ and $\beta$, and spatial smoothness, represented as $\gamma$, as follows.

The similarity constraints, $\alpha$ and $\beta$, are related to the distance and angle of $(p_i, N_a^{pi})$ and $(q_j, N_a^{qj})$. This similarity constraint indicates that if $(p_i, N_a^{pi})$ has smaller distance and angle differences with $(q_j, N_b^{qj})$, then they are more compatible. The disparities between $(p_i, N_a^{pi})$ and $(q_j, N_a^{qj})$ are defined as follows:

$$\alpha(p_i, N_a^{p_i}; q_i, N_a^{q_j}) = \left(1 - \left|\frac{d_i(p_i, N_a^{p_i}) - d_j(q_i N_b^{q_i})}{\max_{i,j}\{d_i(p_i, N_a^{p_i}), d_j(q_i, N_b^{q_j})\}}\right|\right), \text{ and}$$

$$\beta(p_i, N_a^{p_i}; q_i, N_a^{q_j}) = \left(1 - \left|\frac{l_i(p_i, N_a^{p_i}) - l_j(q_i N_b^{q_j})}{\max_{i,j}\{l_i(p_i, N_a^{p_i}), l_j(q_i, N_b^{q_j})\}}\right|\right),$$

where $d_i(\bullet)$ and $l_i(\bullet)$ are the Euclidean distance and angle, respectively.

The second constraint, spatial smoothness $\gamma$, is measured by the distance between $p_i$ and $N_a^{pi}$.

$$\gamma(p_i, N_a^{p_i}) = \left(1 - \frac{d_i(p_i, N_a^{p_i})}{\max_i(d_i(p_i, N_a^{p_i}))}\right),$$

where $$\max_i(d_i(p_i, N_a^{p_i}))$$

is the longest edge of point adjacent point pairs.

Two points $p_i$ and $N_a^{pi}$ are the most salient if $\gamma(p_i, N_a^{pi})$ is one and the least salient if $\gamma(p_i, N_a^{pi})$ is zero. The total compatibility coefficient is defined by: $\tau_{p_iq_j}(N_a^{Pi}N_b^{qj}) = \alpha(p_i, N_a^{Pi}; q_j, N_b^{qi}) \bullet \beta(p_i, N_a^{Pi}; q_j, N_b^{qi}) \bullet \gamma(p_i, N_a^{Pi})$.

Clearly, $\tau_{p_iq_j}(N_a^{Pi}N_b^{qj})$ ranges from zero to one. A high value of $\tau_{p_iq_j}(N_a^{Pi}N_b^{qj})$ corresponds to high matching probability between $(p_i, N_a^{Pi})$ and $(q_j, N_a^{qi})$, and a low value corresponds to incompatibility. The support function $q_{p_iq_j}$ in the k-th iteration is then given by:

$$q_{p_iq_j} = \sum_{i=1}^{I}\sum_{j=1}^{J} r_{p_iq_j}(N_a^{p_i}, N_b^{q_j}) M_{N_a^{p_i},N_b^{q_j}}^k.$$

Note that $r_{p_iq_j}(N_a^{pi},N_b^{qj})$ is weighted by $M_{N_a^{pi},N_b^{qj}}$ because it depends on the likelihood of adjacent point pairs matching probability.

Finally, the fuzzy correspondence matrix M is updated according to:

$$M_{p_iq_j}^{k+1} = M_{p_iq_j}^k q_{p_iq_j}^k \sum_{j=1}^{J} M_{p_iq_j}^k q_{p_iq_j}^k. \quad \text{Equation (20)}$$

The controller uses the relaxation labeling process to update the matrix M continuously until a predetermined stopping criterion is met, so that there is now a point correspondence between the first image of the object and the second image of the object in the matrix $\hat{M}$. The predetermined stopping criteria may be that the E(M) changes less than predetermined amount for new correspondence matrixes M.

The method of FIG. 6 continues with calculating a transformation function using the calculated point correspondence.

Given a correspondence matrix $\hat{M}$ between P and Q, the controller can estimate a transformation $T: R^3 \rightarrow R^3$ that is used to map points from P to Q. In embodiments, a thin-plate spline (TPS) model may be used as disclosed in Chui, et al. 2003 and Bookstein 1989.

The controller may calculate a transformation function from the first image to the second image, f(x, y, z) as follows. Let $v_i$ denote the corresponding location of $p_i=(x_i, y_i, z_i)$, $i=1, 2, \ldots, n$. The controller sets v equal to $x_i'$, $y_i'$, $z_i'$ to obtain continuous transformation for each coordinate. In solving three dimensional interpolation problem, the TPS interpolant f(x, y, z) may be used by the controller to minimize the following bending energy:

$$I_f = \int\int\int\left[\left(\frac{\partial^2 f}{\partial x^2}\right)^2 + \left(\frac{\partial^2 f}{\partial y^2}\right)^2 + \left(\frac{\partial^2 f}{\partial z^2}\right)^2 + 2\left(\left(\frac{\partial^2 f}{\partial x\partial y}\right)^2 + \left(\frac{\partial^2 f}{\partial x\partial z}\right)^2 + \left(\frac{\partial^2 f}{\partial y\partial z}\right)^2\right)\right]dxdydz,$$

The interpolant form is the following Equation (22).

$$f(x, y, z) = \quad \text{Equation (22)}$$
$$a_1 + a_x x + a_y y + a_z z + \sum_{i=1}^{n} w_i U(\|(x_i, y_i, z_i) - (x, y, z)\|).$$

The kernel function U is defined by $U(r)=r^3 \log r^3$. The boundary conditions are $$\sum_{i=1}^{n} w_i = 0 \text{ and } \sum_{i=1}^{n} w_i x_i = \sum_{i=1}^{n} w_i y_i = \sum_{i=1}^{n} w_i z_i = 0.$$

A special characteristic of the TPS is that the resulting transformation can be decomposed by the controller into a global affine transformation component and a local non-affine warping component. In Equation (22), the first four terms of the left hand side describe a global affine transformation and the remaining terms describe a local non-affine transformation. Then the linear sensor for the TPS coefficients can be expressed as follows:

$$\begin{pmatrix} K & P \\ P^T & 0 \end{pmatrix} \begin{pmatrix} W \\ Y \end{pmatrix} = \begin{pmatrix} V \\ 0 \end{pmatrix},$$

$$\text{where } K = \begin{bmatrix} 0 & U(r_{12}) & \ldots & U(r_{1n}) \\ U(r_{21}) & 0 & \ldots & U(r_{2n}) \\ \ldots & \ldots & \ldots & \ldots \\ U(r_{n1}) & U(r_{n2}) & \ldots & 0 \end{bmatrix} \text{ and } P = \begin{bmatrix} 1 & x_1 & y_1 & z_1 \\ 1 & x_2 & y_2 & z_1 \\ \ldots & \ldots & \ldots & \ldots \\ 1 & x_n & y_n & z_1 \end{bmatrix}.$$

Here, $r_{ij}=\|p_i-p_j\|$ is the Euclidean distance between point $p_i$ and $p_j$. W and Y are column vectors formed from $W=(w_1, w_2, \ldots, w_n)^T$ and $Y=(a_1,a_x,a_y,a_z)^T$, respectively. $V=(v_1, v_2, \ldots, v_n)^T$ is any n-vector. If the controller inverts the matrix $$\begin{pmatrix} K & P \\ P^T & 0 \end{pmatrix}$$

and multiplies with matrix $$\begin{pmatrix} V \\ 0 \end{pmatrix},$$

then the coefficients W and Y can be determined. These coefficients determine TPS interpolants $f_x(x,y,z)$, $f_y(x,y,z)$, $f_z(x,y,z)$, which are the x, y, z coordinates of the transformation. The resulting function $f(x, y, z)=|f_x(x, y, z), f_y(x, y, z), f_z(x, y, z)|$ maps each point $(x_i, y_i, y_i)$ to its correspondence point $(x_i', y_i', z_i')$. It provides the controller with a continuous displacement field between $O_1$ and $O_2$.

Thus the controller calculates a transformation function from the first image to the second image, $f(x, y, z)$, using the calculated point correspondence $\hat{M}$ between P and Q.

The method of FIG. 6 continues at 640 with calculating the strain of the object using the calculated transformation function. In embodiments, the controller calculates the non-linear Lagrangian strain tensor component of the uniaxial loading configuration $e_{zz}$ utilizing the following equation:

$$e_{zz} = \frac{\partial f_x(x, y, z)}{\partial z} + \frac{1}{2}\left[\left(\frac{\partial f_x(x, y, z)}{\partial z}\right)^3 + \left(\frac{\partial f_y(x, y, z)}{\partial z}\right)^3 + \left(\frac{\partial f_z(x, y, z)}{\partial z}\right)^3\right].$$

The method of FIG. 6 optionally continues at 650 with calculating the elasticity of the object. To calculate the elastic modulus of the object, the strain component $e_{zz}$ is averaged along the x and y direction to yield the average strain $e_{zz}$-average. The applied normal stress, $S_{ZZ}$, is calculated as described above in Equation (15). The elasticity or elastic modulus E is then determined by the controller using the following equation: $E=S_{ZZ}/e_{zz}$-average.

The controller may display the elastic modulus for human consumption. If the received captured first image and the second image from step 610 are imaged by the tactile sensor being compressed vertically against the object, then Young's modulus will be computed.

If the received captured first image and the second image from step 610 were imaged by the tactile sensor being rubbed or pressed horizontally against the object, then the shear modulus may be calculated by the controller.

Figure 8:
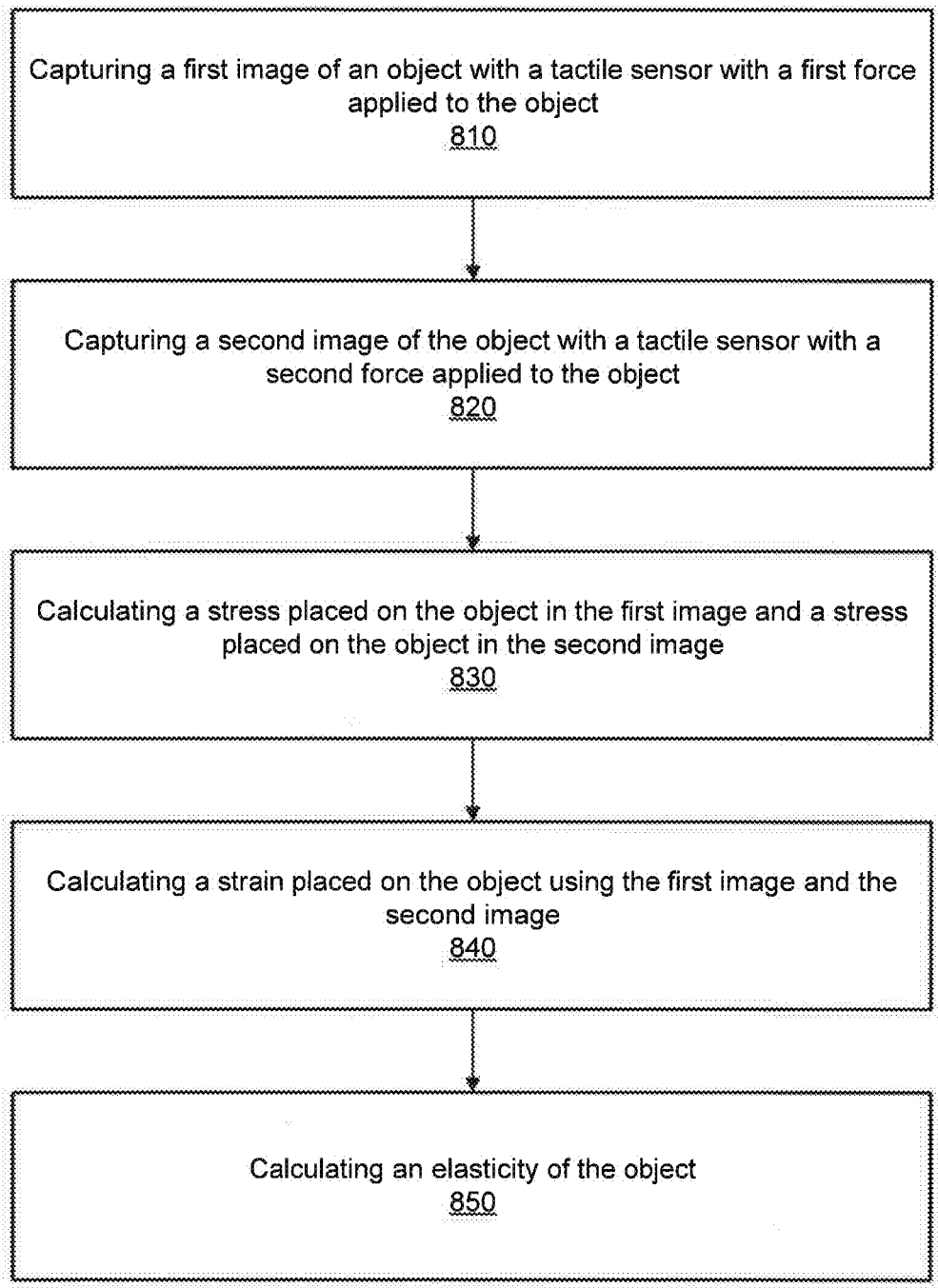
FIG. 8 illustrates an embodiment of a method for calculating the elasticity of an object using a tactile sensor.

FIG. 8 illustrates an embodiment of a method for calculating the elasticity of an object using a tactile sensor of the invention.

The method of FIG. 8 begins at 810 with capturing a first image of an object with a tactile sensor having a first force applied to the object 810. The first force will be in a vertical direction for calculating Young's modulus and in a lateral direction for the calculating shear modulus. The first image may be captured using the tactile sensor described in relation to FIGS. 1 through 4.

The method of FIG. 8 continues at 820 with capturing a second image of the object with a tactile sensor having a second force applied to the object. The second force will be in the vertical direction for calculating Young's modulus and in a lateral direction for calculating the shear modulus. The second image may be captured using the tactile sensor described in relation to FIGS. 1 through 4. The first image and the second image could be captured during a single pressing of an object as the force is increased and/or as the force is decreased. For example, the tactile sensor of FIG. 1 could be pressed into a human breast capturing several images during a continuous pressing and/or multiple images could be captured when pressing the tactile sensor was paused. Additionally, the controller could prompt a user of the tactile sensor to press the object and give instructions for pausing and/or pressing harder or softer on the object and/or removing the tactile sensor and pressing again. The differences between the first image and the second image can be used to calculate a displacement of the object.

The method of FIG. 8 continues at 820 with calculating a stress placed on the object in the first image and a stress placed on the object in the second image. The method discussed in relation to FIG. 5 may be used to calculate the stress placed on the object. One advantage of the tactile sensor as described above is that the force applied to the object may be calculated from the scattered light so that no additional force sensors are required.

The method of FIG. 8 continues at 830 with calculating a strain placed on the object using the first image and the second image. The method described in relation to FIG. 6 may be used to calculate the strain. 3-D reconstructions of the object may need to be calculated. The method described in relation to FIG. 4C may be used to calculate a 3-D reconstruction of the object.

The method may continue at 840 calculating an elasticity of the object. The method used in relation to FIG. 6 may be used to calculate the elasticity of the object. As discussed above, Young's modulus will be calculated if the first force and the second force were applied vertically. The shear modulus will be calculated if the first force and the second force were applied laterally. In embodiments, more than two images may be captured to calculate Young's modulus and the shear modulus. Additionally, values for Young's modulus and the shear modulus may be computed multiple times and averaged, or a medium value may be taken or other statistical methods may be used to obtain a more reliable value. The ratio of Young's modulus to the shear modulus may be used to determine the malignancy of the tumor.

Optionally, the method includes diagnosing the object. The diagnosis may include classifying the object as benign or malignant based on the calculated Young's Modulus, a calculated shear modulus, a calculated size of the object, and a ratio of the calculated Young's Modulus to the calculated shear modulus. The less elastic the object is the more likely the object is not to be benign.

Figure 9A:
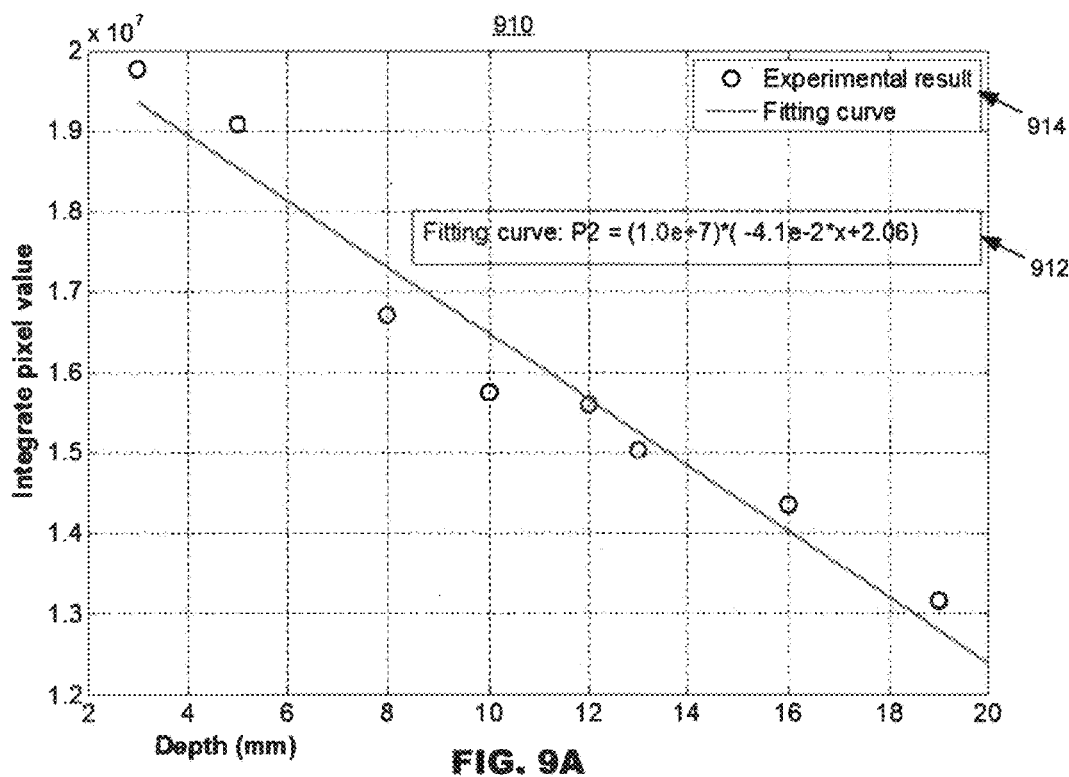
FIG. 9A illustrates a integrated pixel value vs. depth for known sizes of subsurface inclusions in a mouse.

FIG. 9A illustrates a graph of an integrated pixel value vs. depth of subsurface inclusions. An experiment was conducted to determine the relationship between integrated pixel value and depth. A tissue phantom was used of a silicone composite having Young's modulus of approximately 5~10 kPa. Eight subsurface inclusions were placed in the tissue phantom at different depths. Each subsurface inclusion had a diameter of 5.15 mm. The tactile images of each inclusion was obtained under the normal force of between 10 mN and 20 mN. The embodiment of the tactile sensor of FIG. 3B was used for the experiment. Graph 910 illustrates the result of the experiment. As illustrated in the legend 914, the circles are the experimental integrated pixel values calculated for each of the eight subsurface inclusions and the fitting curve 912 is the result of applying a curve fitting method to determine an equation that fits well with the experimental results. The fitting curve 912 for the depth, where H is the depth is given by: $P_2=(-1.0\times10^7)\times(4.1\times10^{-2} H-2.06)$. The equation will vary with the thickness and Young's Modulus of the surrounding tissue.

Figure 9B:
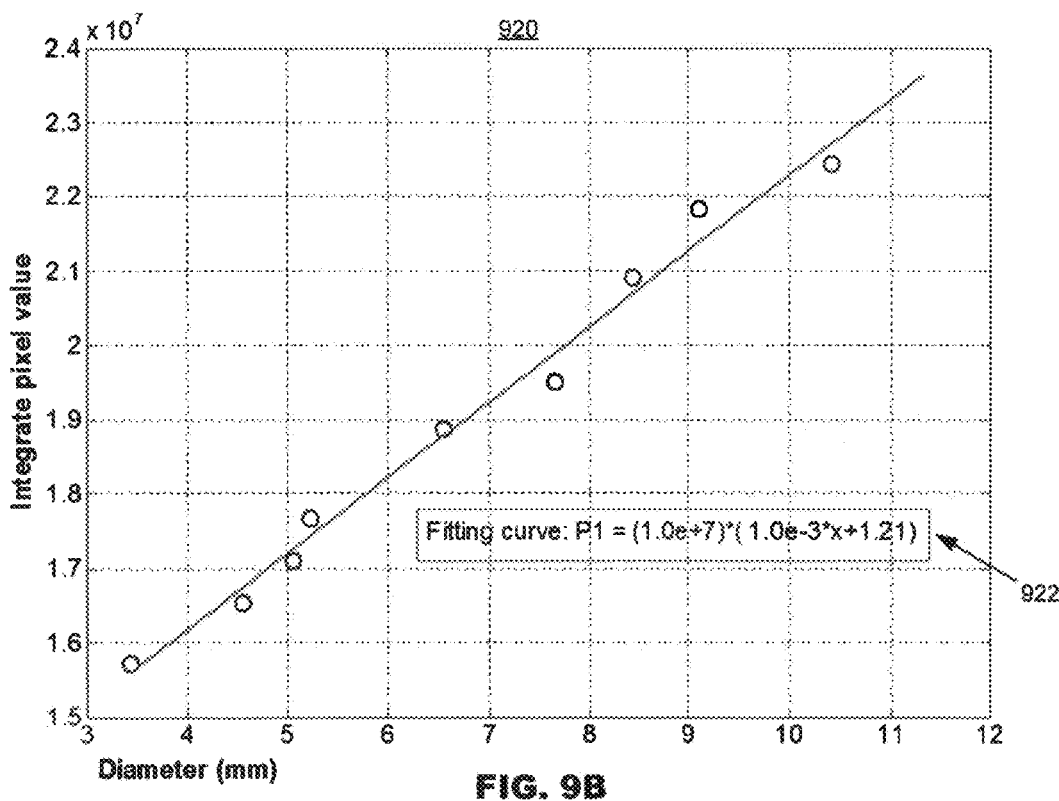
FIG. 9B illustrates a integrated pixel value vs. size for subsurface inclusions with known depths in a mouse.

And FIG. 9B illustrates a graph of an integrated pixel value vs. diameter of subsurface inclusions. The experiment as described above was conducted, except nine subsurface inclusions with different diameters were placed in the phantom tissue at the same depth. Graph 920 illustrates the results of the experiment. The circles are the experimental integrated pixel values calculated for each of the eight subsurface inclusions and the fitting curve 922 is the result of applying a curve fitting method to determine an equation that fits well with the experimental results. The fitting curve 922 for the size, where D is the diameter is given by: $P_1=(1.0\times10^7)\times(1.0\times10^{-3} D+1.21)$. The equation will vary with the thickness and Young's Modulus of the surrounding tissue.

The controller may use equations $P_1$ and $P_2$ to estimate the diameter and depth of a subsurface inclusion. The controller may estimate the Young's Modulus and thickness of the surrounding tissue. In embodiments, the controller may prompt the user for a tissue type and estimate the Young's Modulus based on the response and/or the thickness of the surrounding tissue based on the response.

Figure 10:
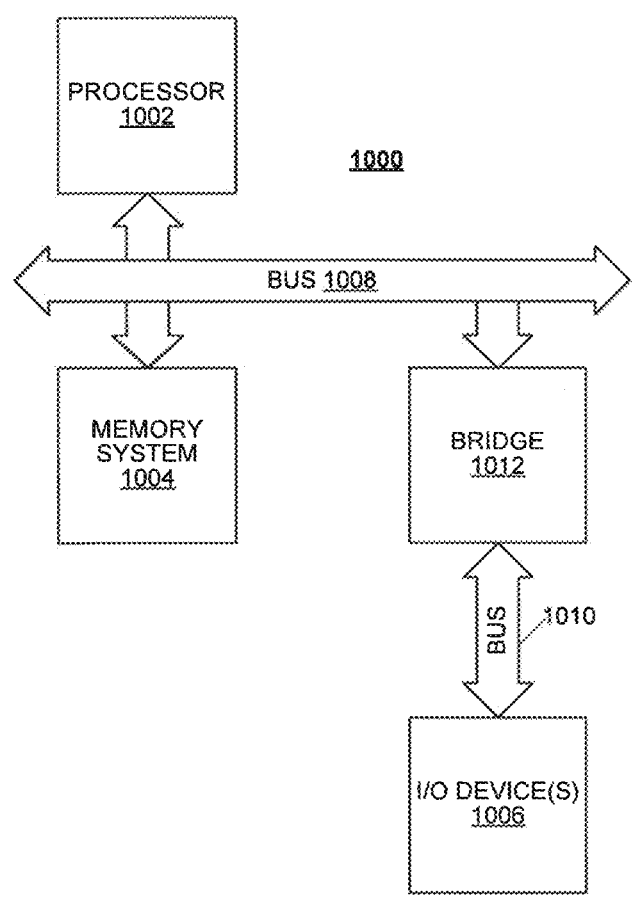
FIG. 10 is a simplified functional block diagram of a computer system.

FIG. 10 is a simplified functional block diagram of a computer system 1000. The controller can be implemented in hardware, software or some combination thereof.

As shown in FIG. 10, the computer system 1000 includes a processor 1002, a memory system 1004 and one or more input/output (I/O) devices 1006 in communication by a communication 'fabric.' The communication fabric can be implemented in a variety of ways and may include one or more computer buses 1008, 1010 and/or bridge devices 1012 as shown in FIG. 10. The I/O devices 1006 can include network adapters and/or mass storage devices. Referring to FIGS. 1 and 10, the controller may be implemented by the computer system 1000 which may receive signals from the light sensor over the network adapters 1006 for processing and then process the signals (for example an image of an object may be generated). The computer system 1000 may send the processed signals over the network adapters 1006 to an I/O device for displaying for human consumption (for example, an image of the object 180 may be displayed on a display 170). The generated signals from the light sensor, the images generated by the controller 160, and modules for performing the various methods discussed above may reside on memory system 1004 and/or on I/O devices 1006. The communication fabric may be in communication with many networks including the Internet and local area networks. The controller 160 may forward the signals from the light sensor and/or images generated by the controller for review and/or processing either locally or remotely or some combination of local and remote processing over the communication fabric.

The apparatuses and methods disclosed herein have better resolution and contrast than ultrasonic methods.

Figure 11:
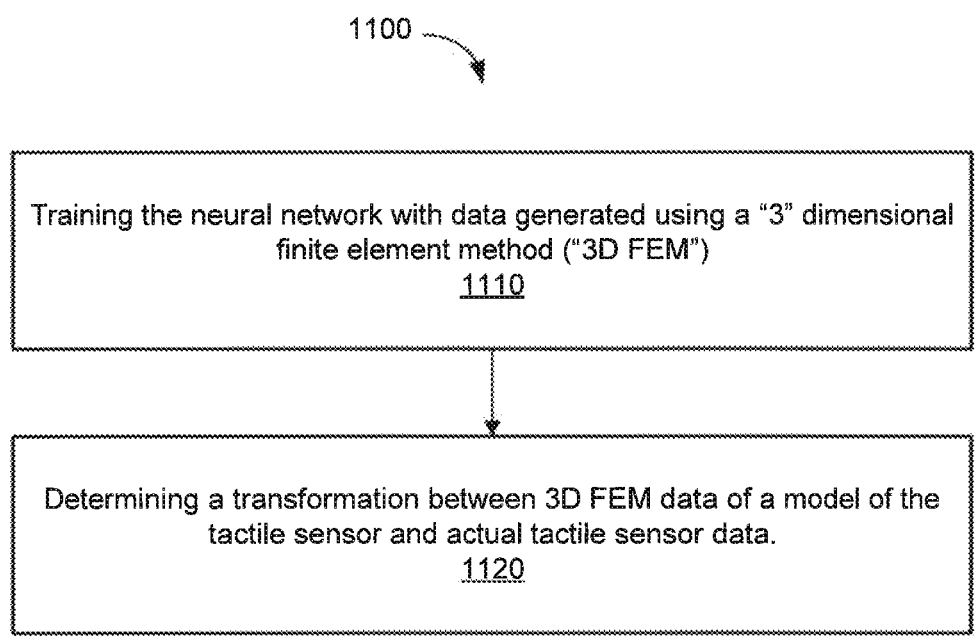
FIG. 11 illustrates a method of training a neural network to determine tissue inclusion parameters from data gathered from a tactile sensor.

FIG. 11 schematically illustrates a method 1100 of training a neural network to determine inclusion parameters from data gathered from a tactile sensor. The inclusion parameters may include the size d, depth h, and the elasticity E, which may be Young's modulus. The data gathered may be from a tactile sensor 100 as disclosed herein. The method 1100 begins at 1110 with training the neural network with data generated using a "3" dimensional finite element method ("3D FEM").

Figure 12:
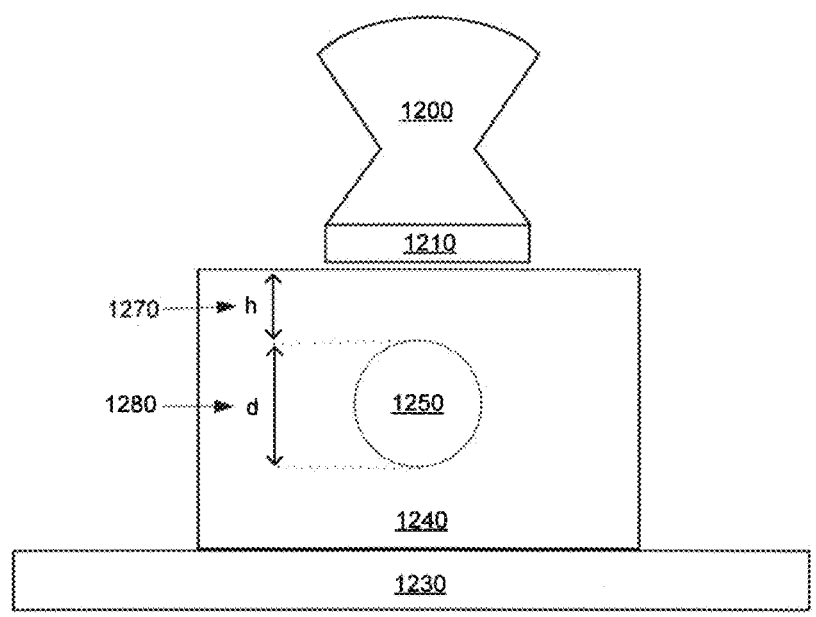
FIG. 12 schematically illustrates a model of idealized breast tissue and a model of a tactile sensor including a model of an optical waveguide, and a model of the object.

The following describes the steps used to generate the data from a 3D FEM to use to train the neural network.
Generating the Data to Train the Neural Network FIG. 12 schematically illustrates a model of idealized breast tissue 1240, a tactile sensor 1200 including a model of an optical waveguide 1210, and the object 1250, which in this case is a model of a subsurface inclusion. The models of the breast tissue 1240, the tactile sensor 1200, and the object 1250, may be manufactured. The model of the subsurface inclusion 1250 has a depth h 1270 from the surface of the model of the tissue 1240, and the model of the subsurface inclusion 1250 has a size d 1280. The following assumptions were used in constructing the model: 1) The model of the breast tissue 1240 is assumed to be a slab of material of constant thickness that is fixed to a model of a flat, incompressible chest wall 1230. 2) The model of the inclusion 1250 is assumed to be spherical. 3) Both the model of tissue 1240 and model of the inclusion 1250 are assumed linear and isotopic. 4) The interaction between the model of the optical waveguide 1210 and the model of the breast tissue 1240 is assumed to be frictionless. See Wellman et al., 2001.

Second, the 3D FEM is used to determine the deformed shape of the modeled optical waveguide 1210 of the tactile sensor 1200 as a result of the model of the tactile sensor 1200 being modeled to press against the model of the breast tissue 1240 with a model of an inclusion 1250. This is repeated multiple times with different parameters of the model of the inclusion 1250. ANSYS™ version 11.0 is used for the 3D FEM. ANSYS™ version 11.0 is an engineering simulation system for building 3D FEMs that is publicly available. A model for the 3D FEM was used with 3,000 finite elements. The following additional assumptions were used for the model of the 3D FEM. 1) The model of the breast tissue 1240 and the model of the inclusion 1250 are elastic and isotropic. This means that the parameters of a material are identical in all directions. 2) The Poisson's ratio of the model of the breast tissue 1240 is set to 0.49 because real breast tissue is elastic. 3) The model of the breast tissue 1240 is assumed to be sitting on an incompressible chest wall 1230.

Figure 13:
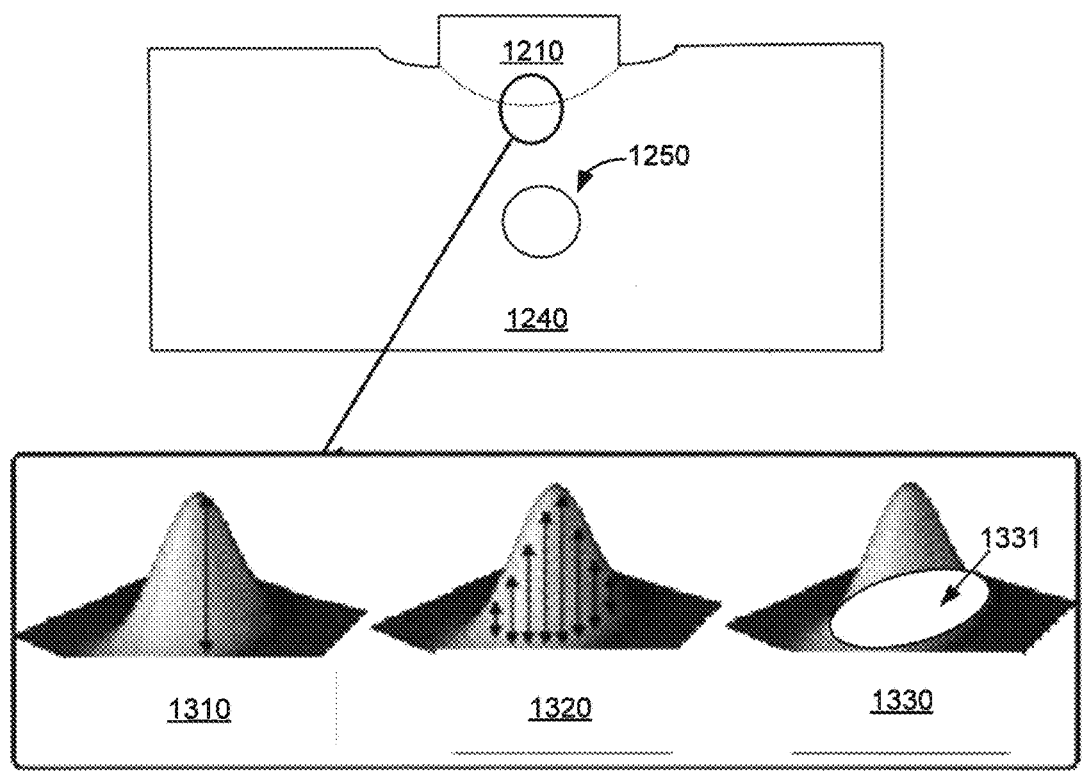
FIG. 13 schematically illustrates the finite element method (FEM) model and the three measures of deformation of the model of the optical waveguide.

FIG. 13 schematically illustrates the FEM model and the three measures of deformation of the model of the optical waveguide 1210. Illustrated is the model of the breast tissue 1240, the model of the inclusion 1250, and the model of the optical waveguide 1210. As illustrated, the model of the optical waveguide 1210 is pressing against the model of the breast tissue 1240, and the model of the optical waveguide 1210 is being deformed because of the model of the inclusion 1250.

Three measures of the deformation of the model of the optical waveguide 1210 are used: maximum deformation $O^1$ 1310, which is defined as the largest displacement of the model of the optical waveguide 1210 from the non-deformed position, total deformation $O^2$ 1320, which is defined as the vertical displacement summation of elements of the model of the waveguide 1210 from the non-deformed position; and, deformation area $O^3$ 1330, which is defined as the projected area 1331 of the deformed surface of the model of the optical waveguide 1210.

Figure 14A:
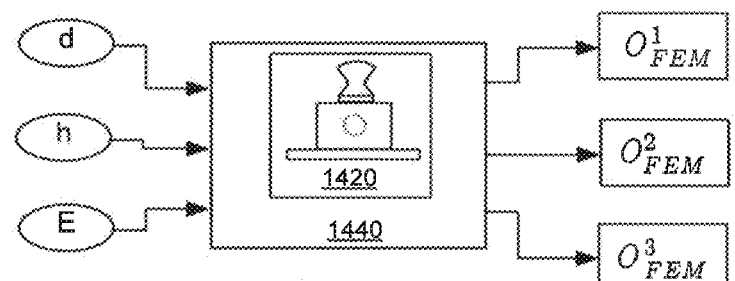
FIG. 14A schematically illustrates generating data to train a neural network with a 3D FEM.

Third, the 3D FEM can then be used to determine $O^i$, $O^2$, and $O^3$ for different d, h, and E values for the model of the inclusion 1250. FIG. 14A schematically illustrates generating data to train a neural network with a 3D FEM. The 3D FEM 1440 is a system for simulation with the models 1420 as discussed above. The input is d, h, and E, and the output is $O^1$, $O^2$, and $O^3$. For example, values of d may be used between 0 mm and 15 mm, and a value of h may be used between 4 mm and 12 mm, and values of E may be used between 40 kPa and 120 kPa. In this way, values for $O^1$, $O^2$, and $O^3$ for the model of the waveguide 1210 can be generated for various values of d, h, and E, using the 3D FEM 1440. As d 1280, the size of the model of the inclusion 1250, increases, the maximum deformation $O^1$ 1310, total deformation $O^2$ 1320, and deformation area $O^3$ 1330, increases; as h 1270, the depth of the model of the inclusion 1250 increases, the maximum deformation $O^1$ 1310, total deformation $O^2$ 1320, and deformation area $O^3$ 1330, decreases, since the model of the waveguide 1210 presses more on the model of the breast tissue 1240 and less on the model of the inclusion 1250. Also, as E the elasticity of the model of the inclusion 1250 increases, the maximum deformation $O^1$ 1310, total deformation $O^2$ 1320, and deformation area $O^3$ 1330, increases, since the model of the inclusion 1250 would then be able to push back more on the model of the waveguide 1210.

Training the Artificial Neural Network

Figure 14B:
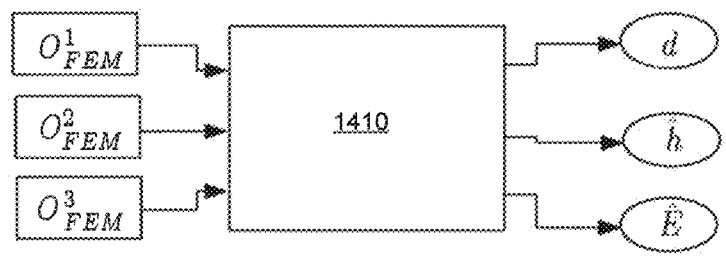
FIG. 14B illustrates a multi-layered artificial neural network (ANN).

After the data is generated the neural network can be trained with the data. Illustrated in FIG. 14B is a multi-layered artificial neural network (ANN) 1410 that takes as input the maximum deformation $O_{FEM}^1$, total deformation $O_{FEM}^2$, and deformation area $O_{FEM}^3$, and generates estimates of the tissue inclusion parameters of size d, depth h, and the elasticity E, which may be Young's modulus. ANN 1410 may comprise neurons united in layers. Each layer is connected with the previous and next layer of the ANN 1410. In an embodiment, the ANN 1410 comprises three layers. The first layer uses 10 neurons with sigmoid activation function. The second layer uses 4 neurons with sigmoid activation function. And, the third layer uses 3 neurons with linear activation function. ANN 1410 is trained using methods known in the art using the data generated from the 3D FEM. In an embodiment, a scaled conjugate gradient algorithm (SCGA) is used to train the ANN 1410.

Determining a Transforming Between 3D FEM Data of a Model of the Tactile Sensor and Actual Tactile Sensor Data The method of FIG. 11 continues at 1120 with determining a transformation between 3D FEM data of a model of the tactile sensor and actual tactile sensor data. The values denoted by $O_{TSIS}^1$, $O_{TSIS}^2$, and $O_{TSIS}^3$ can be calculated by the controller for the real waveguide 110 (see FIGS. 1-3) as follows. $O_{TSIS}^1$ is calculated from the data generated from the waveguide 110 as the maximum pixel value. $O_{TSIS}^2$ is calculated as the summation of the pixel values generated by the real waveguide 110. $O_{TSIS}^3$ is calculated as the number of pixel values generated by the real waveguide 110 above a predetermined threshold value.

A transformation between actual values for $O_{TSIS}^1$, $O_{TSIS}^2$, and $O_{TSIS}^3$, and the modeled values $O_{FEM}^1$, $O_{FEM}^2$, and $O_{FEM}^3$ was determined as follows. A realistic calibration tissue phantom with nine embedded stiff inclusions was manufactured to simulate breast tissue 1240. The nine embedded stiff inclusions were manufactured with different values for d, h, and E. The actual tactile sensor 110 (see FIG. 3B) was then used to generate data for the different nine manufactured inclusions embedded in the manufactured tissue phantom. The result was values for $O_{TSIS}^1$, $O_{TSIS}^2$, and $O_{TSIS}^3$ for each of the nine manufactured inclusions. The 3D FEM model 1440 was then used to generate data for the modeled tactile sensor 1420 for inclusions with the same parameters as the nine manufactured inclusions. The result was values for $O_{FEM}^1$, $O_{FEM}^2$, and $O_{FEM}^3$, for each of the nine manufactured inclusions.

Linear regression methods were used to find a relationship between TSIS data and FEM data so that $O_{TSIS}^1$, $O_{TSIS}^2$, and $O_{TSIS}^3$ data can be transformed to $O_{FEM}^1$, $O_{FEM}^2$, and $O_{FEM}^3$.

Figure 14C:
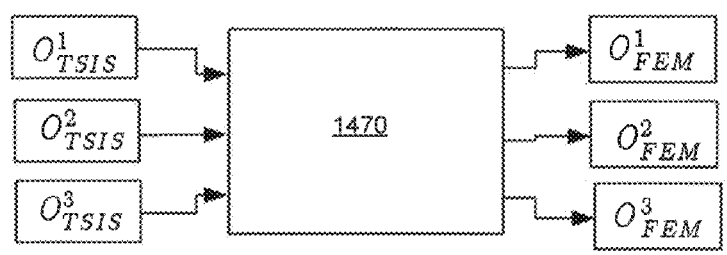
FIG. 14C illustrates deformation parameters collected from an actual tactile sensor being transformed into deformation parameters for a FEM model of a tactile sensor.

The neural network 1410 can be used to estimate parameters of a real inclusion from tactile data gathered from a real tactile sensor by translating the real tactile data to tactile data of the model of the tactile sensor 1420 used in the 3D FEM 1440 as illustrated in FIG. 14C. Actual data is generated by using the tactile sensor 100 on actual breast tissue 140 (FIG. 1) and an actual inclusion 150 (FIG. 1), $O_{TSIS}^1$, $O_{TSIS}^2$, and $O_{TSIS}^3$ are calculated from the actual generated data. $O_{TSIS}^1$, $O_{TSIS}^2$, and $O_{TSIS}^3$ are then transformed into $O_{FEM}^1$, $O_{FEM}^2$, and $O_{FEM}^3$ using the transformation 1470 determined as described above. The values of $O_{FEM}^1$, $O_{FEM}^2$, and $O_{FEM}^3$ are then feed into the trained neural network, for example as illustrated in FIG. 14B, to obtain estimated values for $\hat{d}$, $\hat{h}$, and $\hat{E}$, which are used to estimate the parameters of the actual inclusion 150 (FIG. 1).

Experimental Results for Validating the Training of the Neural Network

FIGS. 15A, 15B, and 15C illustrate a table to validate the method and apparatus. Actual data $O_{TSIS}^1$, $O_{TSIS}^2$, and $O_{TSIS}^3$, was generated by using the tactile sensor 100 on the realistic calibration tissue phantom described above with the nine embedded stiff inclusions. The actual data $O_{TSIS}^1$, $O_{TSIS}^2$, and $O_{TSIS}^3$ is then transformed as described above into $O_{FEM}^1$, $O_{FEM}^2$, and $O_{FEM}^3$ data and then fed into a neural network as illustrated in FIG. 14B which gives estimated values for d, h, and E, denoted as $\hat{d}$, $\hat{h}$, and $\hat{E}$.

The estimated values $\hat{d}$, $\hat{h}$, and $\hat{E}$ were then compared with the actual values of d, h, and E in FIGS. 15A, 15B, and 15C. FIG. 15A is a table 1500 that compares the true size, d 1520, of each of the nine manufactured inclusions 1510 with the est. size, $\hat{d}$ 1530 that was determined by feeding $O_{TSIS}^1$, $O_{TSIS}^2$, and $O_{TSIS}^3$, transformed into $O_{FEM}^1$, $O_{FEM}^2$, and $O_{FEM}^3$, into the neural network 1410 illustrated in FIG. 14b. As illustrated in table 1500, the mean percentage of error between the actual d 1520, and $\hat{d}$ 1530 is 23.93% 1550. Similarly, FIG. 15B illustrates a comparison between actual h and $\hat{h}$, with the result of a mean percentage of error of 39.4% 1560. Similarly, FIG. 15C illustrates a comparison between actual E and $\hat{E}$, with the result of a mean percentage of error of 34.14% 1560.

Thus, a neural network 1410 can be trained to estimate characteristics of an object 150 (see FIG. 1) embedded in tissue 140.

Figure 16:
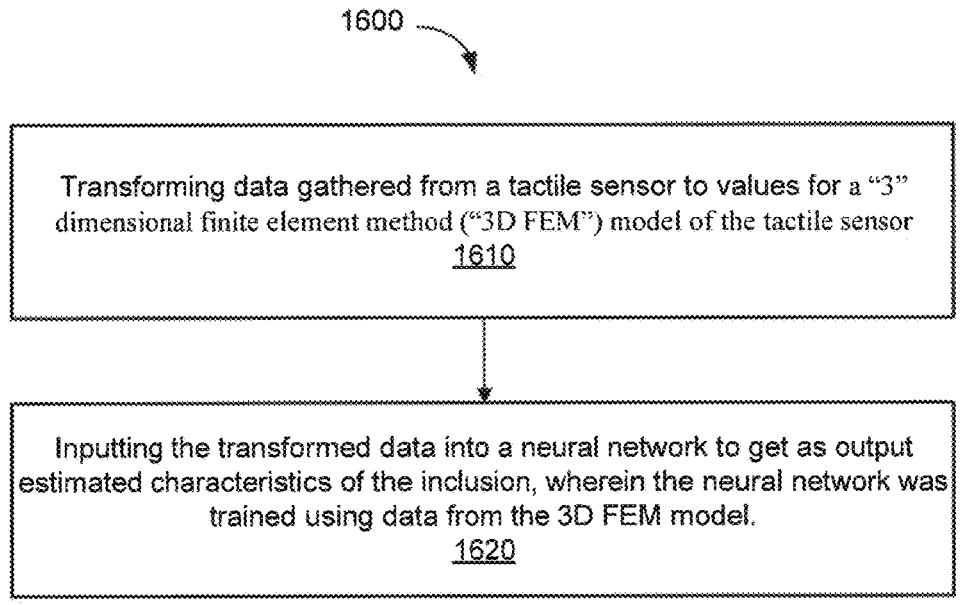
FIG. 16 illustrates a method of determining characteristics of an inclusion.
Figure 17:
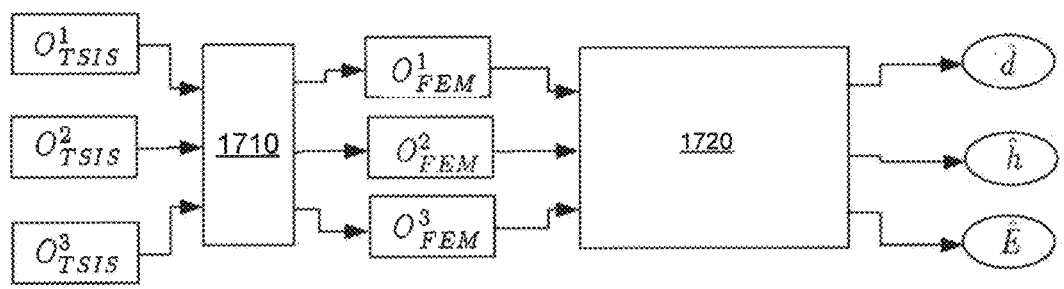
FIG. 17 illustrates data gathered from a tactile sensor.

FIG. 16 illustrates a method 1600 of determining characteristics of an inclusion. The method 1600 begins with transforming data gathered from a tactile sensor to values for a three-dimensional finite-element method ("3D FEM") model of the tactile sensor. As described above, a transformation can be determined between actual tactile sensor data and 3D FEM data of a model of the tactile sensor. Illustrated in FIG. 17 is data gathered from a tactile sensor, $O_{TSIS}^1$, $O_{TSIS}^2$, and $O_{TSIS}^3$, being transformed by a transformation 1710 into values for a 3D FEM, $O_{FEM}^1$, $O_{FEM}^2$, and $O_{FEM}^3$. The values for a 3D FEM are then feed into a neural network 1720 to obtain estimated characteristics of the inclusion, $\hat{d}$, $\hat{h}$, and $\hat{E}$. In embodiments, the characteristics may include diameter, size, depth, mobility, shape, and elasticity.

The method of FIG. 16 continues at 1620 with inputting the transformed data into a neural network to obtain as output, estimated characteristics of the inclusion, wherein the neural network was trained using data from the 3D FEM model. As illustrated in FIG. 17, the transformed data, $O_{FEM}^1$, $O_{FEM}^2$, and $O_{FEM}^3$, can be inputted into a neural network 1720 to obtain estimated characteristics of the inclusion, $\hat{d}$, $\hat{h}$, and $\hat{E}$.

In this way, the characteristics of an inclusion $\hat{d}$, $\hat{h}$, and $\hat{E}$ can be estimated as discussed above with regard to FIGS. 15A, 15B, and 15C.

Inclusion Mechanical Property Estimation Methods Using Tactile Images and Assumptions The following embodiments illustrate estimating mechanical properties of an inclusion 150 from data generated by the tactile sensor 100. The following properties of an inclusion 150 may be estimated from data gathered from the tactile sensor 100: size of the inclusion 150, depth of the inclusion 150, hardness of the inclusion 150, shape of the inclusion 150, and mobility of the inclusion 150.

Inclusion Size

In embodiments, the controller 1002 estimates the size of the inclusion 150 based on a method that assumes that the inclusion 150 is spherical, that there is only one inclusion in the tissue 140, and that there is no noise in the tactile image. The controller 1002 estimates the diameter of an inclusion 150 based on the tactile image 180.

As the diameter of an inclusion increases, the light scattering increases as the effect of a larger inclusion causes the optical waveguide to deform more. Thus, the light scattering area of an image may be used by the controller 160 to estimate the size of the inclusion 150 (see FIG. 1.) The controller 160 may calculate the size of an inclusion as follows. If I(x,y) denote an individual pixel value on the light sensor 130, then the light scattering area, denoted A, captured on the light sensor 130 is calculated by the controller 160 by counting the number of pixels larger than a predetermined constant, denoted k, as follows in Equation (23).

$$A = \text{Number of pixel values greater than } k. \quad \text{Equation (23):}$$

The area, A, in Equation (23) is the pixel area on the light sensor 130. To transform the pixel area, A, of the light sensor 130 to the area of the inclusion 150, the controller 160 uses a scale factor. In an embodiment, the controller 160 uses a scale factor between the actual area of the object 150 and the image pixel area of the light sensor 130 of $(6.79 \times 10^{-3})^2$ mm² per pixel area. This scale factor was obtained by calibration of the invention.

A relative diameter, denoted di, of a tissue inclusion is calculated by the controller 160 as follows in Equation (24).

$$di = 2\sqrt{(6.79 \times 10^{-3})^2 \times A / \pi}. \quad \text{Equation (24):}$$

Inclusion Depth Estimation

The controller 160 (see FIG. 1) estimates the depth of an object 150 based on the pixel values from the light sensor 130.

As the depth of an object 150 increases, the light scattering due to the waveguide 110 deformation decreases because the object 150 presses less against the waveguide 110. Since it is assumed in this embodiment, that the object 150 is spherical, the pixel values at the light sensor 130 distribute in a bell shape, and the pixel intensity of the light sensor 130 that is the highest is assumed by the controller 160 to correspond to the centroid of the object 150. Thus, the controller 1002 calculates the estimated relative inclusion depth based on pixel values of the light sensor 130.

Figure 18:
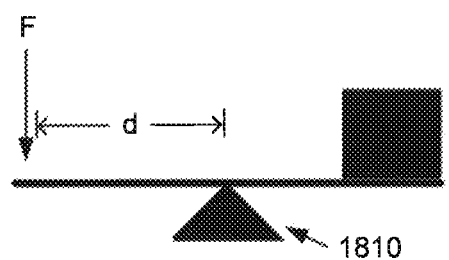
FIG. 18 illustrates the moment (M) of a force (F) about some fixed fulcrum.

A moment, denoted M, due to the force of pressing the waveguide 110 (FIG. 1) on the tissue 140 with the inclusion 150, can be calculated by the controller 160 as schematically illustrated in FIG. 18. The controller 160 may calculate the moment M of a force F about some fixed fulcrum 1810 as illustrated in FIG. 18, and according to Equation (25) by force (F) times distance (d).

$$M = F*d, \text{ where } d \text{ is the distance from the fulcrum} \\ 1810 \text{ to the line of action of the force } F. \quad \text{Equation (25):}$$

The controller 160 can calculate depth, denoted h (see FIG. 12) of the inclusion 150 as follows.

Figure 19:
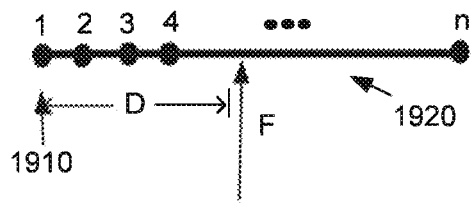
FIG. 19 illustrates a system of n point masses situated along a horizontal line.

A system of n point masses situated along a horizontal line, as schematically illustrated in FIG. 19, are assumed to be attached to a rigid weightless framework 1920 with a pivot point at the left end 1910. If the weights of the masses are $w_1$, $w_2$, $w_3$, ... $w_n$ and their distances from the pivot point are $x_1$, $x_2$, $x_3$, ... $x_n$, then the sum of the clockwise moments of the n masses with respect to the pivot point, denoted $M_i$, may be calculated according to Equations (26) and (27).

$$M_1 = w_1 x_1 + w_2 x_2 + w_3 x_3 + \ldots w_n x_n, \quad \text{Equation (26):}$$

$$Fd = w_1 x_1 + w_2 x_2 + w_3 x_3 + \ldots + w_n x_n, \quad \text{Equation (27):}$$

where F is the equivalent force and d is the equivalent distance for all the weights. Thus, d may be calculated according to Equation (28).

$$2\sqrt{(6.79 \times 10^{-3})^2 \times A/\pi} \quad \text{Equation (28)}$$
$$d = \frac{w_1 x_1 | w_2 x_2 | w_3 x_3 | \cdots w_n x_n}{w_1 + w_2 + w_3 + \cdots w_n}.$$

Equation (28) is extended to centroids of x and y coordinates of the tactile image. The pixels of the light sensor 130 with the greatest intensity are assumed to correspond to the centroid of the object 150. Since the light sensor 130 is 2-dimensional, the x and y coordinates of the centroid of the object 150, denoted $(X_C, Y_C)$ ($X_c$, $Y_c$), is calculated according to Equations (29) and (30).

$$X_c = \frac{\iint_{x,y} I(x, y) x \, dx \, dy}{\iint_{x,y} I(x, y) \, dx \, dy}, \quad \text{Equation (29)}$$

$$Y_c = \frac{\iint_{x,y} I(x, y) y \, dx \, dy}{\iint_{x,y} I(x, y) \, dx \, dy}. \quad \text{Equation (30)}$$

$X_C$ and $Y_C$ are the moment, M, in the x or y direction divided by the force (sum of the weights). Then a relative depth of an inclusion h is calculated by the controller 160 according to Equation (31).

$$h = I(X_C, Y_C). \qquad \text{Equation (31):}$$

Equation (31) assumes that the intensity of the tactile image is only a function of the depth of the inclusion, even though intensity is a function of hardness and depth. Since the calculated depth is the pixel distance, using the scale fact $6.79 \times 10^{-3}$ mm per pixel distance, the controller 1102 can transform the pixel distance to the actual distance.

Inclusion Hardness Estimation

The "hardness" of the inclusion may be expressed by Young's modulus E. Young's modulus is expressed as stress over strain as in Equation (32) below.

$$E = \text{stress/strain}. \qquad \text{Equation (32):}$$

The controller 160 (see FIG. 1) measures stress as force per unit area. The controller 160 estimates the force F using the integrated pixel value of the tactile image as discussed herein. The function is given by Equation (33).

$$\text{normal force } [mN] = \frac{\text{integrated pixel values}}{1.4778 \times 10^6} - 3.7894 \times 10^{-8}$$

$$\text{normal force } [mN] = \frac{\text{pixel summation}}{1.4778 \times 10^6} - 0.37894. \qquad \text{Equation (33)}$$

The controller 160 can calculate the stress of the inclusion using Equation (34).

$$\text{stress} = \text{normal force/contact area}. \qquad \text{Equation (34):}$$

The other value needed to calculate the elastic modulus is the strain. The strain is the change in a size of the inclusion in response to a force applied to the inclusion. To find the strain T, the controller 160 obtains two tactile images 180 using two different forces as described above. The controller 160, then calculates the diameters of an object 150 for the two different tactile images 180 using Equation (24) to derive $d_1$ and $d_2$. The strain is calculated by the controller 160 as the change in diameter $\Delta d$ over $d_1$ according to Equation (35).

$$\text{strain} = \frac{\Delta d}{d_1} \quad \text{strain} = \frac{\Delta d}{d_1}, \text{ where } \Delta d = d_1 - d_2^{d_1 - d_2}. \qquad \text{Equation (35)}$$

The obtained stress and strain are used by the controller 160 to estimate the relative hardness of a tissue inclusion as discussed above.

Inclusion Shape Estimation

The controller 160 (see FIG. 1) may estimate the tissue inclusion shape by separating an image into regions (on their contours). Thresholding as described below is used by the controller 160 to perform image segmentation. A grayscale tactile image is obtained by the controller 160 and thresholding is used to create binary images. Thresholding is a process whereby the controller 160 marks individual pixels in the tactile image as "object" pixels if their value is greater than a threshold value, which assumes an object 150 to be brighter than the background, and marks pixels as "background" pixels if the pixels are below the threshold value. Typically, an object pixel is given a value of one while a background pixel is given a value of zero. Finally, a binary tactile image is created by coloring each pixel white or black, depending on a pixel's label. If $g(x,y)$ is a threshold version of $I(x,y)$, an image I, with a threshold value of T, then the controller 160 may estimate the shape according to Equation (36).

$$g(x,y) = 1 \text{ if } I(x,y) \geq T \text{ and } 0 \text{ otherwise.} \qquad \text{Equation (36):}$$

In an embodiment, a thresholding method of clustering using K-means variation may be used by the controller 160. The controller 160 separates the pixels of the image, $I(x,y)$, into two clusters (object and background). T denotes the threshold, $\mu_B(T)$ denotes the mean of all pixel values $I(x,y)$ less than the threshold T, and $\mu_O(T)$ denotes the mean of all pixel values greater than the threshold T.

The controller 160 calculates a threshold T such that Equations (37) and (38) are true.

$$\forall I(x,y) \geq T: |I(x,y) - \mu_B(T)| \geq |I(x,y) - \mu_O(T)|, \text{ and} \qquad \text{Equation (37):}$$

$$\forall I(x,y) < T: |I(x,y) - \mu_B(T)| < |I(x,y) - \mu_O(T)|. \qquad \text{Equation (38):}$$

The controller 160 uses a method where $\mu_B(T)$ is set to the average of the four corner pixels (assumed to be background) and $\mu_O(T)$ is set to the average of the remaining pixels. The controller 160 sets T to be halfway between $\mu_B(T)$ and $\mu_O(T)$. The controller 160 then separates the pixels according to how close their intensities are to $\mu_B(T)$ and $\mu_O(T)$. The controller 160 then updates the estimates of $\mu_B(T)$ and $\mu_O(T)$ by calculating the mean of the pixel values on each side of the threshold T, and by reducing the threshold T. The controller 160 then may repeat this process until the threshold T is below a predetermined level and until the controller 160 labels all image pixels into "object" or "background". From this method, the controller 160 segments the "object" and the "background". Based on the segmented image of the "object", the controller 1002 can estimate the shape of the object by using methods known in the art, such as matching with predetermined shapes.

Inclusion Mobility Estimation

The tactile sensor 100 (see FIG. 1) may obtain multiple images without moving the tactile sensor 100. The controller 160 may calculate the mobility of the object 150 as a Euclidean distance between calculated centroids $(X_C, Y_C)$ ⌊$(X^\uparrow_c, Y_c)$ of the object 150 from tactile images obtained at different times, denoted t. The tactile images may be obtained by continuously pressing the tactile sensor 100 on the tissue 140. If the tactile image centroid of a tactile image that is obtained at time t−1 is denoted as $(X_{C_{t-1}}, Y_{C_{t-1}})$, ⌊$(X^\uparrow_{C_{t-1}}, Y_{C_{t-1}})$ and the centroid of tactile image that is obtained at time t is noted as $(X_{C_t}, Y_{C_t})$ ⌊$(X^\uparrow_{c_t}, Y_{c_t})$, then the controller 160 calculates the mobility, denoted M, according to Equation (39).

$$M = \sqrt{|X_{c_t} - X_{c_{t-1}}|^2 \; |Y_{c_t} - Y_{c_{t-1}}|^2} \cdot \qquad \text{Equation (39)}$$

$$\sqrt{\left[\square|X_{c_t} - X|_{c_{t-1}}\right]^2 + \left[\square|Y_{c_t} - Y|_{c_{t-1}}\right]^2} \cdot$$

The mobility of the tissue inclusion is estimated as a Euclidean distance between the tactile image centroids $(X_{C_{t-1}}, Y_{C_{t-1}})$ and $(X_{C_t}, Y_{C_t})$. A longer Euclidean distance implies a larger mobility, and a shorter Euclidean distance implies smaller mobility of the inclusions.

Figure 20:
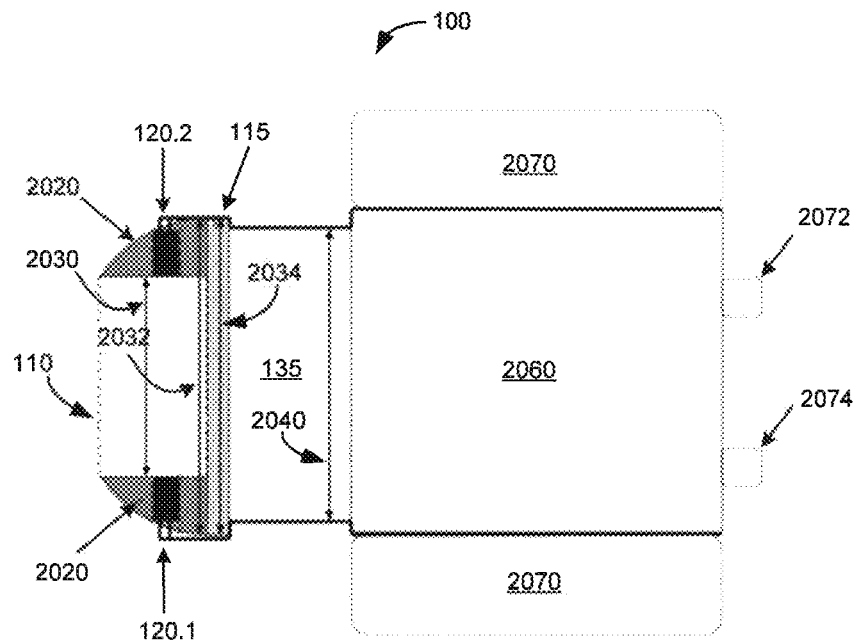
FIG. 20 illustrates an embodiment of the tactile sensor.

FIG. 20 illustrates an embodiment of the tactile sensor, which includes an optical waveguide 110, light sources 120.1 and 120.2, camera body 2060, lens 135, rigid layer 115, frame 2020, power source 2070, communication port 2072, and light intensity switch 2074. The embodiment illustrated may be manufactured from a digital camera. The following describes a particular embodiment of the tactile sensor 100 illustrated in FIG. 20 with dimensions all of which are approximate.

In the embodiment illustrated, the frame 2020 is a wooden-half sphere of 1.75 inches diameter. The frame may be in a shape suitable for the application. For example, the frame may be shaped in a rectangular, square, or polygonal shape. The frame will support the waveguide and light sources. The frame 2020 is drilled in five locations (See FIG. 21): one hole to house the optical waveguide 110, and four holes for the light sources 120. Only two of the four light sources 120 are illustrated in FIG. 20. The half sphere design of the frame 2020 has the benefit of permitting detection of inclusions 150 at a greater depth, d. The half sphere design of the frame 2020 has a diameter 2032 of 44.45 mm (1.75 inches). The cutout diameter 2030 of the frame 2020 is 25.4 mm (1 inch). The light sources 120 are 3 mm (0.12 inches) in diameter. The rigid layer 115 is a round glass plate with a diameter of 38.1 mm (1.5 inches). The lens 135 has a diameter of 30 mm (1.18 inches). The communication port 2072 may support one or more communication protocols between the data gathered by the optical waveguide 110 and an external device (not illustrated). An example of a communication protocol is "fire wire." The optical waveguide 110 is circular in shape to fit snuggly in the frame 2020. The optical waveguide 110 may be a membrane that is flexible and transparent and may have a height of less than 1 mm. The membrane 119 may be replaceable and may be replaced for hygienic reasons.

Figure 21:
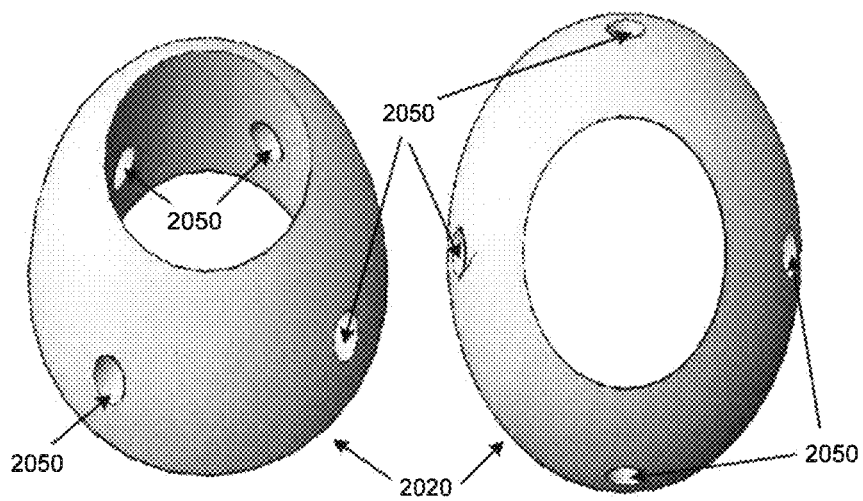
FIG. 21 schematically illustrates a frame.

FIG. 21 schematically illustrates frame 2020, which is a wooden-half sphere of 1.75 inches diameter. The frame 2020 may be manufactured of another suitable material to house the optical waveguide 110 and the light sources 120. The frame 2020 may be altered in shape so that it is not spherical as long as it is another suitable shape. The frame 2020 includes four cut-outs 2050 for light sources 120 and one cut-out for the optical waveguide 110.

The optical waveguide 110 may be manufactured by the following process. The following describes an embodiment of the optical waveguide 110 comprising PDMS as illustrated in FIG. 21. One specific type of PDMS is room temperature vulcanizing (RTV) silicone dielectric gels, which may be used to mimic the flexibility of human skin. RTVs are low viscosity liquid silicones which cure at room temperature to form very soft gel-like elastomers. Two component materials (A and B) of RTV are supplied where A is a base agent and B is a curing agent. The objective of the method is to prepare PMDS by mixing A and B.

The following equipment may be utilized in performing the method. One cylindrical shape hydrometer jar (mold) with an outer diameter of 14 mm and an inner diameter 13 mm, which may be made of PDMS and more particularly of polymethylpentene (PMP). One PDMS mold with a rectangular cuboid shape, which may be a medication organizer with each cell being of 25 mm by 20 mm by 14 mm. As much silicone dielectric gel as needed in the form of RTV with two components A and B. A bench scale to electronically balance measured the silicone dielectric gel. One stirring rod to stir the A and B components. A knife to cut the cylindrical shaped mold. Plastic glasses can be used as a container for mixing components A and B.

Cured properties of silicone gel can be ensured if they are mixed at a ratio of 1:1 (by weight). Increasing the ratio of part A to part B will yield a softer gel (i.e. more flexible) whereas decreasing the ratio of part A to part B will result in a gel that is less flexible.

The following method may be performed to manufacture the waveguide 110. The method of FIG. 22 begins with step 2201 placing a mold according to the desired waveguide shape on the scale which will result in the mass of the mold being displayed. The zero button may be pressed so that the balance will reset to zero and ignore the mass of the mold so that only the weight of liquid A and B will be shown on the display. The method of FIG. 22 continues with step 2202 while keeping the mold on the scale pour A and B components with the desired ratio. The method continues with step 2203 stirring the mixture for five minutes. The method continues with step 2204 keeping the mixture for one day at room temperature. The method continues with step 2205 of cutting the sides and bottom of the mold carefully to produce a homogeneous mixture.

The method is applicable for single ratio mixing for cylindrical or rectangular cuboid mold. For preparation of a waveguide 110 with multiple layers with different flexibility and refractive indexes such as is illustrated in FIG. 3A repeat the steps 2201, 2202, 2203, and 2204 for each of the layers with the appropriate mixtures of A and B. The weight of the mixture components A and B will depend upon frame size and shape. The shape may be semispherical, rectangular cuboid, or another suitable shape.

Additional Experiments

Figure 22:
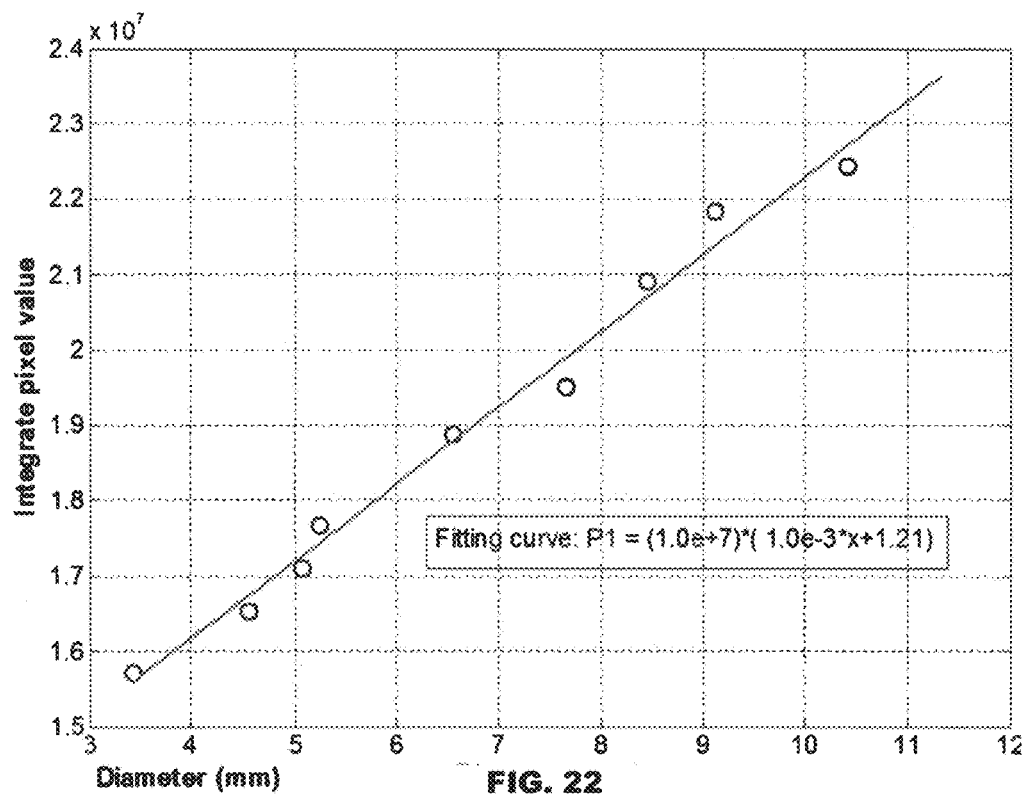
FIG. 22 illustrates the integrated pixel value of the tactile image along the diameter of the inclusions.
Figure 23:
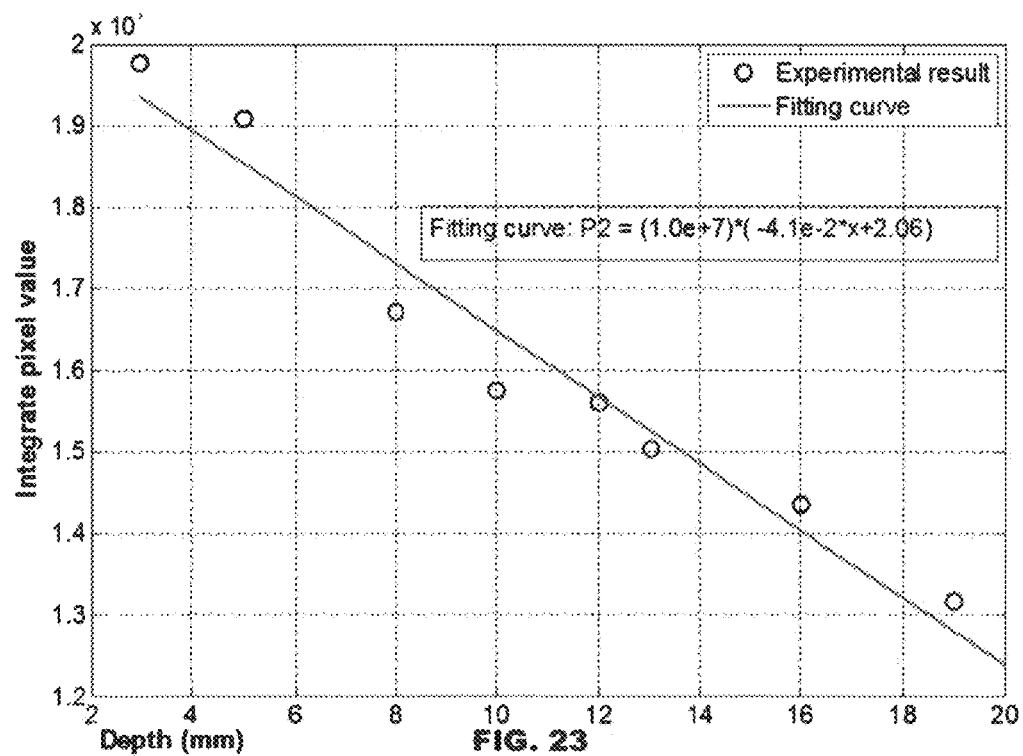
FIG. 23 illustrates the integrated pixel value of the tactile image along the depth of the inclusions.

A tissue phantom 1240 (see FIG. 12) with embedded simulated tumor 1250 was manufactured. The phantom 1240 was made of a silicone composite having Young's modulus of approximately 5~10 kPa. To find the relation between tactile imaging device 100 and inclusion diameter 1250, a total of nine inclusions 1250 with different diameters were placed below the surface of the phantom 1240. The depth of each inclusion 1250 was 4.2 mm. The inclusion 1250 was manufactured using another silicone composite, the stiffness of which was much higher (300~500 kPa) than the surrounding tissue phantom 1240. To find the relation between tactile imaging device 100 and inclusion depth, eight inclusions 1250 were placed in the tissue phantom 1240 with varying depth. The diameter of each inclusion was 5.15 mm. The tactile images 180 of each inclusion were obtained under the normal force of between 10 mN and 20 mN. FIG. 22 illustrates the integrated pixel value of the tactile image 180 along the diameter of the inclusions 1250 and FIG. 23 illustrates the integrated pixel value of the tactile image 180 along the depth of the inclusions 1250.

The inclusion parameter (i.e. diameter and depth) estimation using the obtained tactile image 180 can be formulated as an inversion problem. The integrated pixel value of tactile image 180 is taken as input for the problem. For the inclusion diameter estimation experiments, two inclusions 1250 were embedded into the phantom 1240 with the same depths of 4.2 mm. After taking tactile images 180, the diameters were estimated using the first order approximation curve $P1=(1.0e+7)*(1.0e-3*x+1.21)$ in FIG. 22. Similarly, for the depth estimation experiments, two inclusions 1250 with the same diameters of 5.15 mm were embedded and the depths have been estimated using the first order approximation curve $P2=(1.0e+7)*(-4.1e-2*x+2.06)$ in FIG. 23. The results illustrate that the embodiment of the invention used to perform the tests estimates the inclusion diameter within 4.09% and the inclusion depth within 7.55% error.

For the following discussion see FIGS. 1 and 2. The embodiment of the sensor 100 used in the additional experiments and the mouse experiments is as follows. The sensor 100 comprises an optical waveguide 110, a digital imager 130, light sources 120, and piano-convex lens 135. The optical waveguide 110 was composed of PDMS with three layers 110.1, 110.2, 110.3. The elastic moduli of each PDMS layer 110.1, 110.2, 110.3, was set to the moduli values of epidermis (elastic coefficient $1.4 \times 10^5$ Pa), dermis ($8.0 \times 10^4$ Pa) and subcutanea ($3.4 \times 10^4$ Pa), respectively, of a human finger to realize sensitivity to the level of the human touch sensation. The light sensor 130 was a mono-cooled complementary camera with 8.4 μm (H)×9.8 μm (V) individual pixel size. The maximum lens resolution was 768 (H)×492 (V) with an angle of view of 60°. The light sensor 130 was placed below an optical waveguide 110. A heat-resistant borosilicate glass plate 115 was placed as a substrate between the light sensor 130 and the optical waveguide 110 to sustain it without losing resolution. The glass plate 115 emulates the bone or the nail in the human finger. The internal light source 120 is a micro-LED 120 with a diameter of 1.8 mm. There were four LEDs 120 used on four sides of the waveguide 110 to provide illumination. The direction and incident angle of light sources 120 were calibrated with the cone of an acceptance angle for the total internal reflection in a waveguide. The plano-convex lenses 135 was used for the light coupling between the waveguide 110 and light sources 120.

Mice Experiments

Figure 24A:
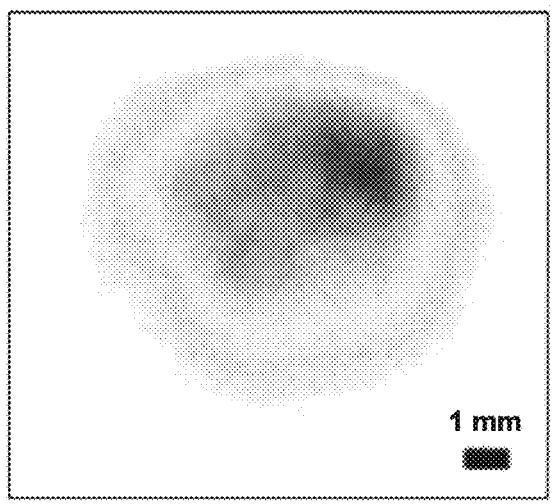
FIGS. 24A, 24B, and 25 illustrate tactile images of three different globus tumors grown in a mouse.
Figure 24B:
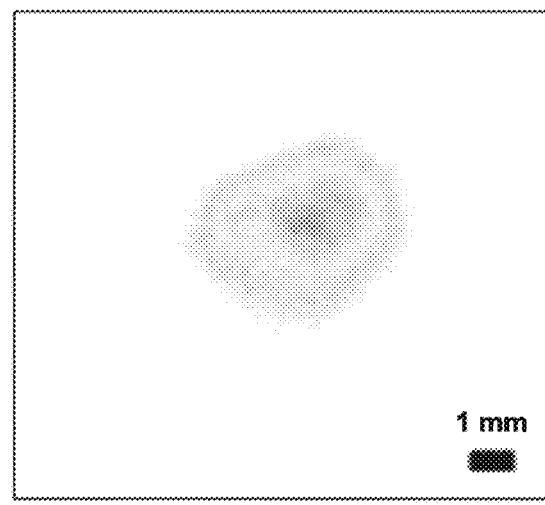
Figure 25:
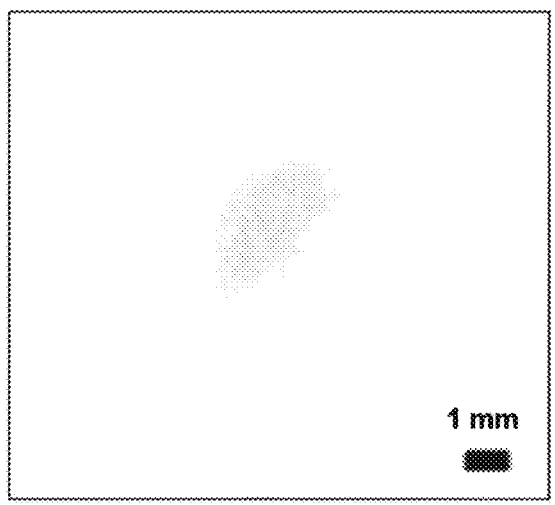

Inclusion detection experiments were also performed using mice with objects 150 that were globus tumors. Three different tumors 150 were grown in real mice and imaged using the tactile sensor 100 described above. The sizes of the tumors were 15.23 mm×10.28 mm (target 1), 7.20 mm×6.32 mm (target 2), and 3.84 mm×2.74 mm (target 3). FIGS. 24A, 24B, and 25, respectively, illustrate the tactile images 150 of three different globus tumors grown in a mouse. The target 3 2500 was small and it was very difficult to detect by hand, but the tactile image device 100 detected it as illustrated in FIG. 25.

The mice experiment results illustrate that an embodiment of the invention successfully detects the tumors 150 with the tumor 150 being as small as 2.74 mm.

Experimental Results for Multiple Layer Waveguide Vs. Single Layer Waveguide

Figure 26:
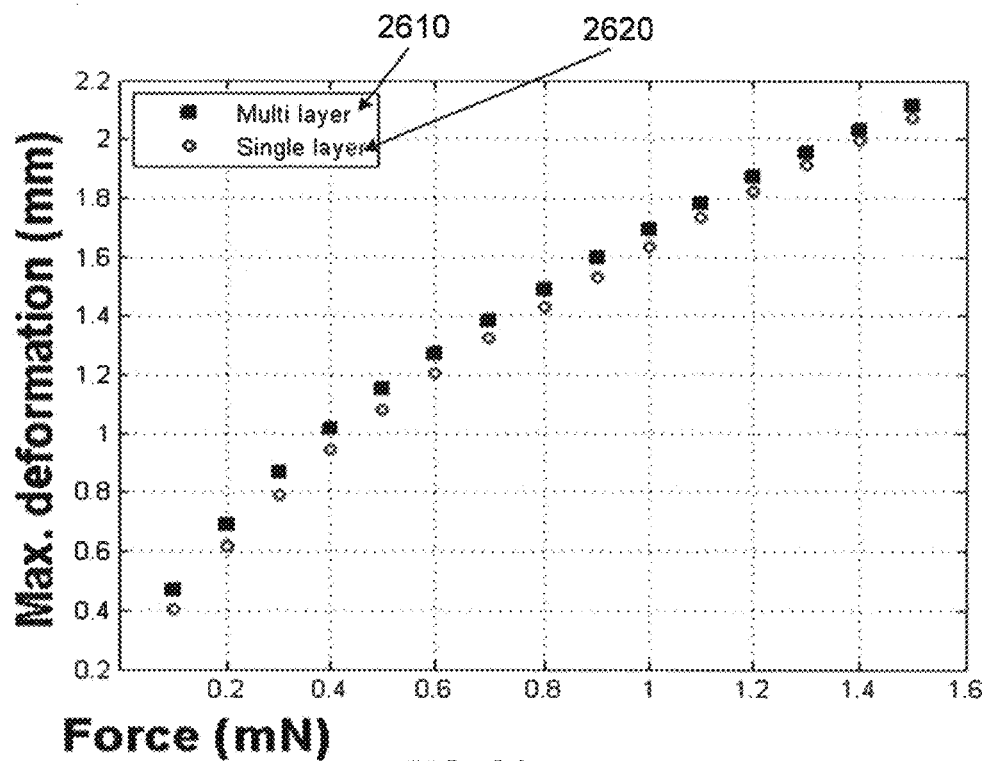
FIG. 26 illustrates the difference in maximum deformation between a single layer tactile sensor and a three layer tactile sensor.

FIG. 26 illustrates experimental results for the difference in maximum deformation between a tactile sensor with a single layer waveguide and a tactile sensor with a multiple layer waveguide. The data from the tactile sensor with a multiple layer waveguide 2610 is represented with squares, and the data from the tactile sensor with a single layer waveguide 2620 is represented with circles. The force ranged from 0 mN to 1.6 mN. The maximum deformation was determined by determining the largest pixel intensity value of the waveguide 2610, 2620 and then determining the distance (mm) of deformation of the waveguide 2610, 2620 at the place of the waveguide 2610, 2620 where the largest pixel intensity value was determined. The multiple layer waveguide 2610 comprised three layers with moduli E1, E2, E3, and depths, L1, L2, L3, respectively. The single layer waveguide 2620 was constructed to have an effective modulus, $E_{eff}$, which was calculated as follows:

$$E_{eff}=(L1+L2+L3)/(L1/E1+L2/E2+L3/E3).$$

Based on the experimental results, the multiple layer waveguide 2610 is more sensitive than the single layer waveguide 2620; however, the single layer waveguide 2620 may be adequate for many applications that do not require the additional sensitivity of the multi layer waveguide 2610.

Figure 27:
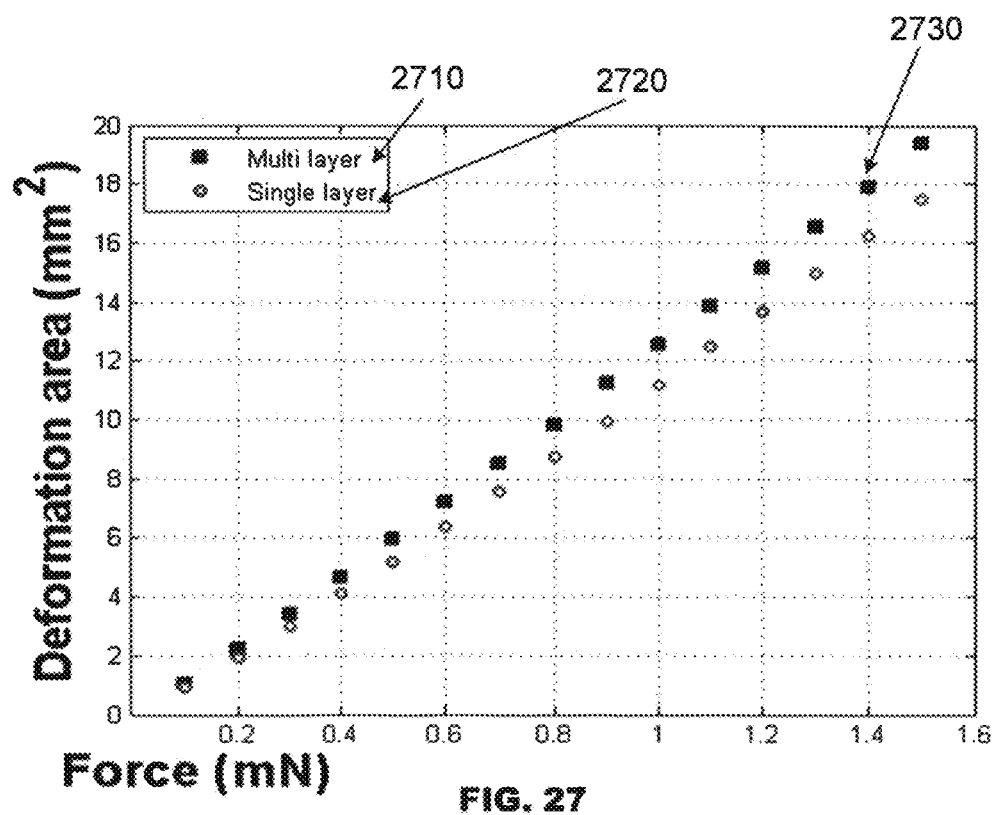
FIG. 27 illustrates the difference in total deformation between a single layer tactile sensor and a three layer tactile sensor.

FIG. 27 illustrates experimental results for the difference in total deformation between a tactile sensor with a single layer waveguide and a tactile sensor with multiple layer waveguide. The data from the tactile sensor with a multiple layer waveguide 2710 is represented with squares, and the data from the tactile sensor with a single layer waveguide 2720 is represented with circles. The force ranged from 0 mN to 1.6 mN. The total deformation was determined as the area of the waveguide (millimeters squared) 2710, 2720 that had a positive pixel value. Three layers were used for the multiple layer waveguide 2710. As the force applied to the waveguides 2710, 2720 increased the difference between the deformation of the single layer waveguide 2720 and multiple layer waveguide 2710 increased. For larger forces there was some difference between the single layer waveguide 2720 and the multiple layer waveguide 2710. At 1.4 mN (element 2730) the deformation area was 16.1 mm² for the single layer waveguide 2720 and 18 mm² for the multiple layer waveguide 2710.

The experiment results indicate that the multiple waveguide 2710 is more sensitive to a change in force applied to the waveguide than the single layer waveguide 2720. Consequently, depending on the sensitivity needed based on the application of the tactile sensor, either a single layer waveguide 2720 or a multiple layer waveguide 2710 could be used for the tactile sensor.

The optical waveguide may be formed into various shapes suitable for pressing against tissue 140. Example shapes include a sheet, an oval, a polygon, a disk, and a two sided shape. In some embodiments, the optical waveguide may be used to image objects in material other than tissue 140. The tissue 140 (see FIG. 1) may be any tissue such as a human breast, skin, thyroid, or prostate, that may contain an object 150, which in this case is a subsurface inclusion. In embodiments, the optical waveguide may not be transparent. The width and length of the optical waveguide may vary depending on the application, for example, from 2 millimeters to 50 centimeters may be used. For example, in embodiments, a large 50 cm by 50 cm waveguide may be used for breast cancer screening.

In embodiments, the light sensor 130 (see FIG. 1) may be an imager. In embodiments, the rigid layer 115 (see FIG. 1) may be composed of, for example, glass or plastic, or another suitable material. Although the tactile sensor described herein is an exemplary embodiment designed for use with tissue, it should be noted that the tactile sensor can be utilized for other applications of imaging objects embedded in materials different from tissue.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of instructions on a machine readable medium and/or computer readable medium, which may be in a physical form.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion. Also, functional programs, codes, and code segments for accomplishing the present invention can be easily construed by programmers skilled in the art to which the present invention pertains. The computer readable recording medium may be non-transitory.

The use of the terms "a" and "an" and "the" and similar referents in the context of describing the invention (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

Although described in connection with preferred embodiments thereof, it will be appreciated by those skilled in the art that additions, deletions, modifications, and substitutions not specifically described may be made without departure from the spirit and scope of the invention as defined in the appended claims.

Belongie, S., Malik, J. and Puzicha, J, "Shape matching and object recognition using shape contexts," IEEE Trans. Pattern Anal. and Mach. Intell., vol. 24, no. 4, pp. 509-522, 2000.

Bluemke D. A., Gatsonis, C. A., Chen, M. H., et al., (2004) "Magnetic resonance imaging of the breast prior to biopsy," Journal of the American Medical Association, vol. 292, no. 22, pp. 2735-2742.

Bookstein, F. L., "Principal warps: thin-plate spline and the decomposition of deformations," IEEE Trans. Pattern Anal. and Mach. Intell., vol. 11, no. 6, pp. 567-585, 1989.

Carney, P. A., Miglioretti, D. L., Yankaskas, B. C., et al., (2003) "Individual and combined effects of age, breast density, and hormone replacement therapy use on the accuracy of screening mammography," Annals of Internal Medicine, vol. 138, no. 3, pp. 168-175.

Chui, H. and Rangarajan, A., "A new point matching algorithm for non-Rigid registration," Comput. Vis. Image Und., vol. 23, no. 2-3, pp. 114-141, 2003.

Dargahi, J. and Najarian, S., "Human tactile perception as a standard for artificial tactile sensing—a review," Int. J. Med. Robot. Comput. Assist. Surg., vol. 1, no. 1, pp. 23-35, 2004.

Galea, A. M., "Mapping tactile imaging information: parameter estimation and deformable registration," Ph.D. dissertation, School of Engineering and Applied Sciences, Harvard University.

Garra, B., Cespedes, E., Ophir, J., Spratt, S., Zuurbier, R., Magnant, C., and Pennanen, M., (1997), "Elastography of Breast Lesions: Initial Clinical Results," Radiology, Vol. 202, No. 1, pp. 79-86.

Greenleaf, J. F., Fatemi, M., Insana, M., (2003) "Selected Methods for Imaging Elastic Properties of Biological Tissues," Annu. Rev. Biomed. Eng., Vol. 5, pp. 57-78.

Hall, T., (2003), "Beyond the Basics: Elasticity Imaging with US," Radio Graphics, Vol. 23, No. 6, pp. 1657-1671.

Insana, M. F., Pellot-Barakat, C., Sridhar, M., and Lindfors, K. K., "Viscoelastic imaging of breast tumor microenvironment with ultrasound," Journal of Mammary Gland Biology and Neoplasia, vol. 9, num. 4, pp. 393-404, 2004.

Jatoi I. (2003) "Screening clinical breast examination," The Surgical Clinics of North America, Elsevier, Vol. 83, No. 4, pp. 789-801.

Pelillo, M., and Refice, M., "Learning compatibility coefficients for relaxation labeling processes," IEEE Trans. Pattern Anal. and Mach. Intell, vol. 16, no. 9, pp. 933-945, 1994.

Raza, S. and Baum, J. K., (1997) "Solid breast lesions: evaluation with power Doppler US," Radiology, vol. 203, no. 1, pp. 164-168.

Regini, E., Bagnera, S., Tota, D., Campanino, P., Luparia, A., Barisone, F., Durando, M., Mariscotti, G., and Gandini, G., "Role of sonoelastography in characterising breast nodules. Preliminary experience with 120 lesions," Radiol. Med., vol. 115, no. 4, pp. 551-562, 2010.

Sinkhorn, R., "A relaxation Between Arbitrary Positive Matrices and Doubly Sochastic Matrices," The Annals of Mathematical Statistics, vol. 35, pp. 876-879, 1964.

Stravros, A., Thickman, D., Dennis, M., Parker, S., Sisney, G., (1995), "Solid Breast Nodules: Use of Sonography to Distinguish between Benign and Malignant Lesions," Radiology, Vol. 196, No. 1, pp. 79-86.

Vinckier, A., and Semenza, G., "Measuring elasticity of biological materials by atomic force microscopy," FEBS Letters, vol. 430, no. 1-2, pp. 12-16, 1998.

Wellman, P. S., Howe, R. D., Dalton, E., and Kern, K. A., (1999), "Breast Tissue Stiffness in Comparison is Correlated to Histological Diagnosis," Harvard Robotics Laboratory Technical Report.

Wellman, P. S., Dalton, E. P, Krag, D., Kern, K., Howe, R. D., (2001), "Tactile Imaging of Breast Masses: First Clinical Report," Archives of Surgery, Vol. 136, No. 2, pp. 204-208.

Wilson, L. S., Robinson, D. E., Dadd, M. J., (2000) "Elastography-Movement Begins," Phys. Med. In Biology, Vol. 45, pp-1409-1421.

The entire disclosure of each document cited herein is incorporated herein by reference. All references, including publications, patent applications, and patents, cited herein are hereby incorporated by reference to the same extent as if each reference were individually and specifically indicated to be incorporated by reference and were set forth in its entirety herein.

What is claimed is:

1. A tactile sensor for generating an image of an object, the tactile sensor comprising:
   an optical waveguide comprised of at least a first portion that is flexible and a second portion that is adjacent to the first portion and provides the optical waveguide with rigidity, wherein at least part of the first portion is transparent so as to permit light to pass out of the first portion and into the second portion;
   at least two sources of light configured to direct light into the optical waveguide, one of the light sources being mounted to a side of the waveguide opposite from the other light source such that when activated each of the light sources directs light into the waveguide toward the other light source; and
   a light sensor facing the optical waveguide and configured to generate signals from light scattered out of the optical waveguide,
   wherein the waveguide is configured so that at least some of the light directed into the optical waveguide is scattered out of the first portion when the first portion is deformed, and wherein the first portion is deformed by the tactile sensor being pressed against the object.

2. The tactile sensor of claim 1 wherein the second portion is a frame positioned between the first portion and the light sensor.

3. The tactile sensor of claim 2 wherein the frame supports the first portion of the optical waveguide around a circumference of the optical waveguide.

4. The tactile sensor of claim 3 wherein the frame is opaque.

5. The tactile sensor of claim 1 wherein the second portion is a rigid transparent layer that permits passage of light from the first portion to the light sensor.

6. The tactile sensor of claim 1 wherein the optical waveguide has a shape suitable for pressing against tissue, and wherein the shape of the optical waveguide provides rigidity for supporting the flexibility of the first portion.

7. The tactile sensor of claim 6 wherein the shape is planar, oval, polygonal, or disk.

8. The tactile sensor of claim 7 wherein the second portion is planar.

9. The tactile sensor of claim 1 wherein the second portion has a different refractive index than a refractive index of the first portion.

10. The tactile sensor of claim 9 wherein the refractive index of the second portion is less than the refractive index of the first portion.

11. The tactile sensor of claim 1 wherein the first portion and the second portion are the same material.

12. The tactile sensor of claim 1 wherein the first portion and the second portion are different materials.

13. The tactile sensor of claim 12 wherein the first portion is silicone elastomer and the second portion is glass or plastic.

14. The tactile sensor of claim 13 wherein the silicone elastomer is PDMS.

15. The tactile sensor of claim 1, further comprising a diffuser associated with each light source for diffusing the light emitted by the light source.

16. The tactile sensor of claim 1, further comprising a controller configured to calculate and display a physical characteristic of the object based on changes in the light received by the light sensor.

17. A method for calculating an elasticity of an object using a tactile sensor, the method comprising:
   capturing a first image of the object with the tactile sensor comprising:
      an optical waveguide comprised of at least a flexible first portion that is at least partially transparent so as to permit light to pass out of the first portion;
      at least one source of light configured to direct light into the optical waveguide; and
      a light sensor facing the optical waveguide and configured to generate signals from light scattered out of the optical waveguide,
      wherein the waveguide is configured so that at least some of the light directed into the optical waveguide is scattered out of the first portion when the first portion is deformed, and wherein the first portion is deformed by the tactile sensor being pressed against the object with a first force applied to the object;
   capturing a second image of the object with the tactile sensor wherein the first portion is deformed by the tactile sensor being pressed against the object with a second force applied to the object;
   calculating a stress placed on the object in the first image and a stress placed on the object in the second image;
   calculating a strain placed on the object using the first image and the second image; and
   calculating an elasticity of the object.

18. A tactile sensor for generating an image of an object, the tactile sensor comprising:
   an optical waveguide comprised of at least a flexible first portion that is at least partially transparent so as to permit light to pass out of the first portion;
   at least two sources of light configured to direct light into the optical waveguide, one of the light sources being mounted to a side of the waveguide opposite from the other light source such that when activated each of the light sources directs light into the waveguide toward the other light source;
   a light sensor facing the optical waveguide and configured to generate signals from light scattered out of the optical waveguide; and
   a controller configured to display an image of the object based on the signals from the light sensor,
   wherein the waveguide is configured so that at least some of the light directed into the optical waveguide is scattered out of the first portion when the first portion is deformed, and wherein the first portion is deformed by the tactile sensor being pressed against the object.

19. The tactile sensor of claim 18, wherein the optical waveguide further comprises a second portion that is adjacent to the first portion and provides the optical waveguide with rigidity, wherein light to passes out of the first portion and into the second portion.

20. The tactile sensor of claim 18, further comprising a diffuser associated with each light source for diffusing the light emitted by the light source.

21. A tactile sensor for generating an image of an object, the tactile sensor comprising:
   an optical waveguide comprised of at least a first portion that is flexible and a second portion that is adjacent to the first portion and provides the optical waveguide with rigidity, wherein at least part of the first portion is transparent so as to permit light to pass out of the first portion and into the second portion;

at least one source of light configured to direct light into the optical waveguide; and a light sensor facing the optical waveguide and configured to generate signals from light scattered out of the optical waveguide, wherein the waveguide is configured so that at least some of the light directed into the optical waveguide is scattered out of the first portion when the first portion is deformed, and wherein the first portion is deformed by the tactile sensor being pressed against the object further comprising a controller configured to determine and display at least one of an elasticity of the object, a hardness of the object, a Young's Modulus of the object, a shear modulus of the object, and a malignancy determination of the object.

22. The tactile sensor of claim 21 wherein the controller is further configured to diagnose the object based on a ratio of a calculated Young's Modulus to a calculated shear modulus.

23. The tactile sensor of claim 21, further comprising a diffuser to diffuse the light emitted by the light source.

24. The tactile sensor of claim 21 wherein the controller is further configured to compare a captured first image of the object having a first force applied to the object with a captured second image of the object having a second force applied to the object and to calculate the elasticity of the object based on comparing the object in the first image with the object in the second image and based on the first force and the second force.

* * * * *